US005670507A

United States Patent [19]
Rice et al.

[11] Patent Number: 5,670,507
[45] Date of Patent: Sep. 23, 1997

[54] METHOD FOR REVERSING MULTIPLE DRUG RESISTANT PHENOTYPE

[75] Inventors: Glenn C. Rice; Jack W. Singer, both of Seattle, Wash.

[73] Assignee: Cell Therapeutics, Inc., Seattle, Wash.

[21] Appl. No.: 379,232

[22] Filed: Jan. 27, 1995

[51] Int. Cl.⁶ .................. A61K 31/52; A61K 31/565; A61K 31/44; A61K 31/47
[52] U.S. Cl. .................. 514/263; 514/274; 514/299; 514/310; 514/315; 514/418
[58] Field of Search .................. 514/263, 183, 514/558, 310, 258, 262, 274, 299, 315, 418

[56] References Cited

FOREIGN PATENT DOCUMENTS

WO94.22863  10/1994  WIPO .................. C07D 473/10

OTHER PUBLICATIONS

Yang et al., *Cancer Res.* 54:730, 1994.
Endicott and Ling, *Ann. Rev. Biochem.* 58:137, 1989.
Bellamy et al., *Cancer Invest.* 8:547, 1990.
Twentyman, *Anticancer Res.* 8:985, 1988.
Yusa and Tsuruo, *Cancer Res.* 49:5002, 1989.
Léonce et al., *Biochem. Pharmacology* 44:1707, 1992.
Arceci et al., *Blood* 80:1528, 1992.
Merlin et al., *Blood.* 84:262, 1994.
Weaver et al., *Int. J. Cancer* 54:456, 1993.
Boesch et al., *Exp. Cell Res.* 196:26, 1991.
Chan et al., *Hematology/Oncology Clinics North Amer.*8:383, 1994.

*Primary Examiner*—John W. Rollins
*Attorney, Agent, or Firm*—Foley & Lardner

[57] ABSTRACT

There is disclosed a method for reversing the multiple drug resistant (MDR) phenotype in tumors insensitive to hydrophobic chemotherapeutic drugs due to over expression of mdr-1, comprising administering an effective amount of a long chain amino alcohol compound. There is further disclosed a method for preventing the development of MDR during cancer chemotherapy treatments, comprising administering during cancer chemotherapy treatments an effective amount of a long chain amino alcohol compound.

6 Claims, 10 Drawing Sheets

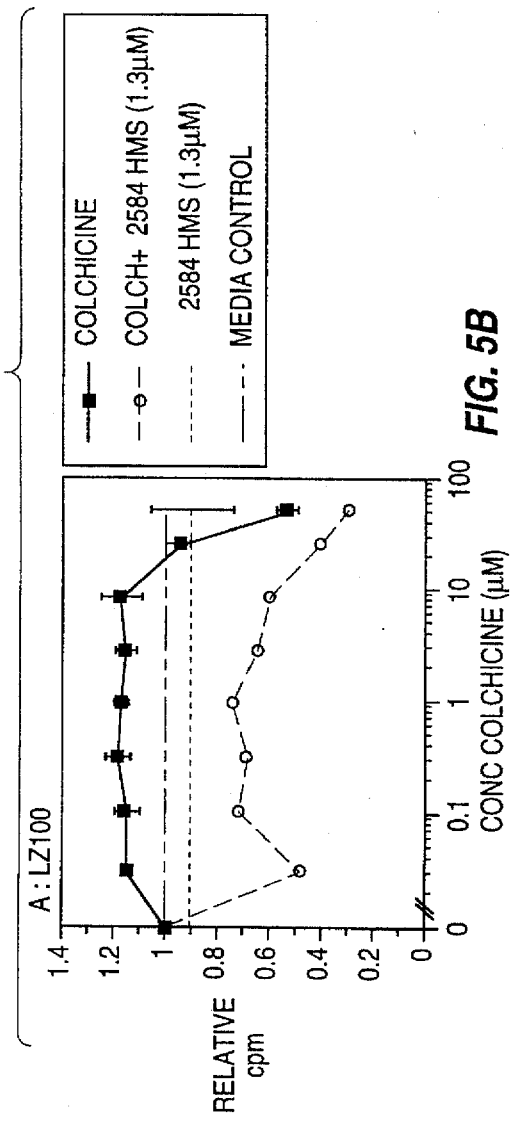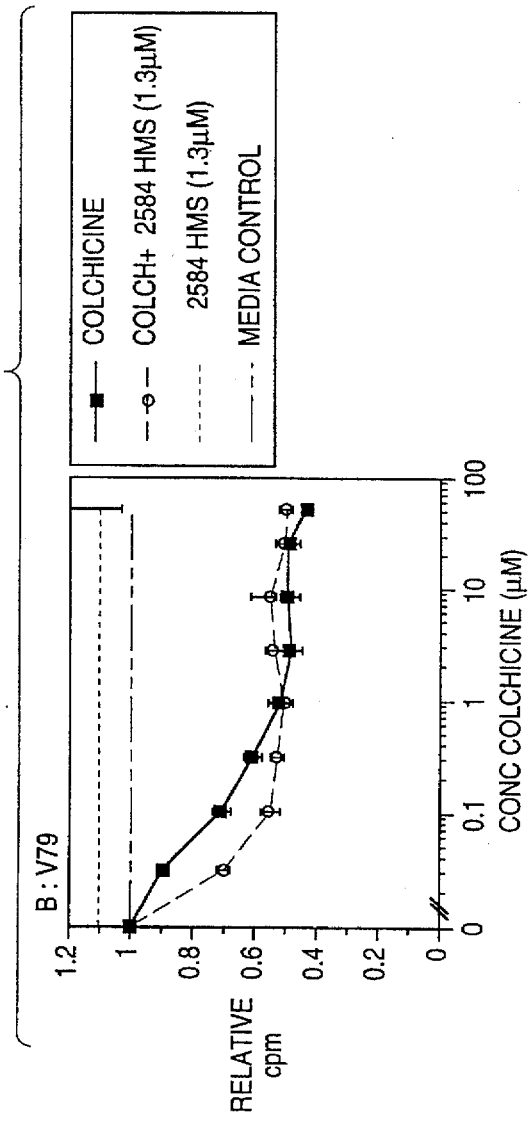
FIG. 5A
FIG. 5B

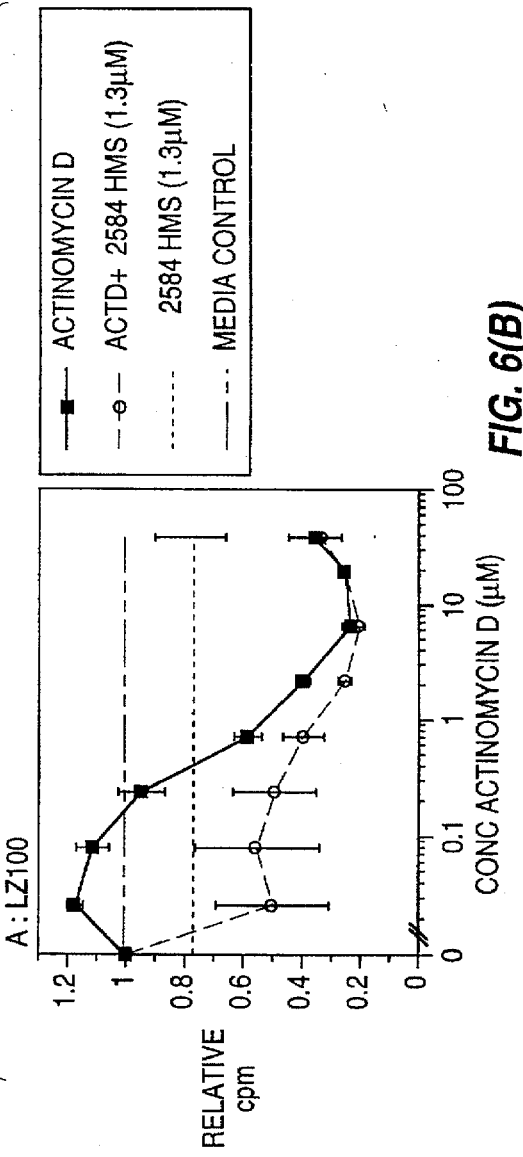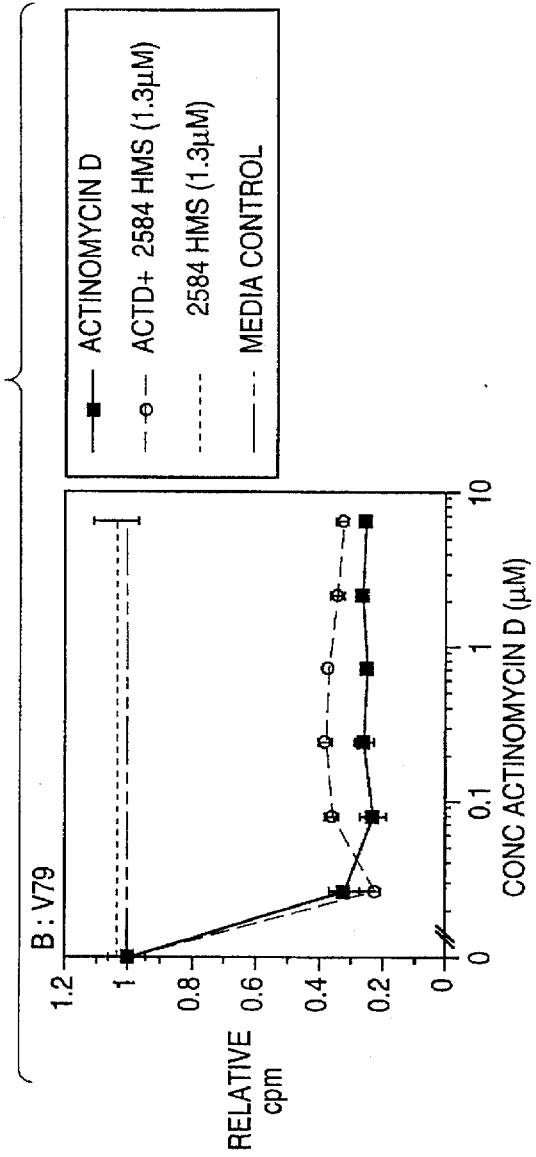
FIG. 6(A)
FIG. 6(B)

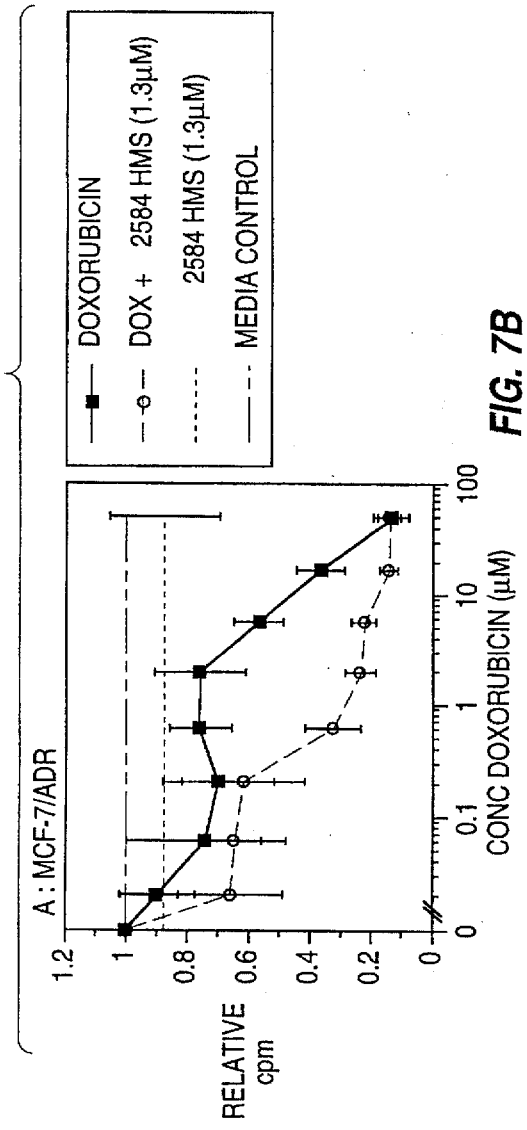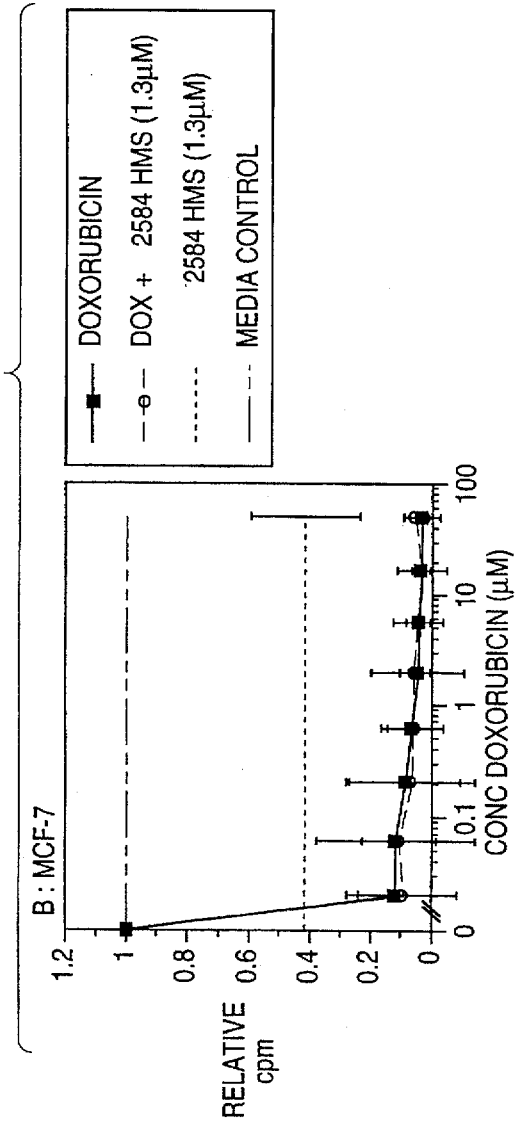

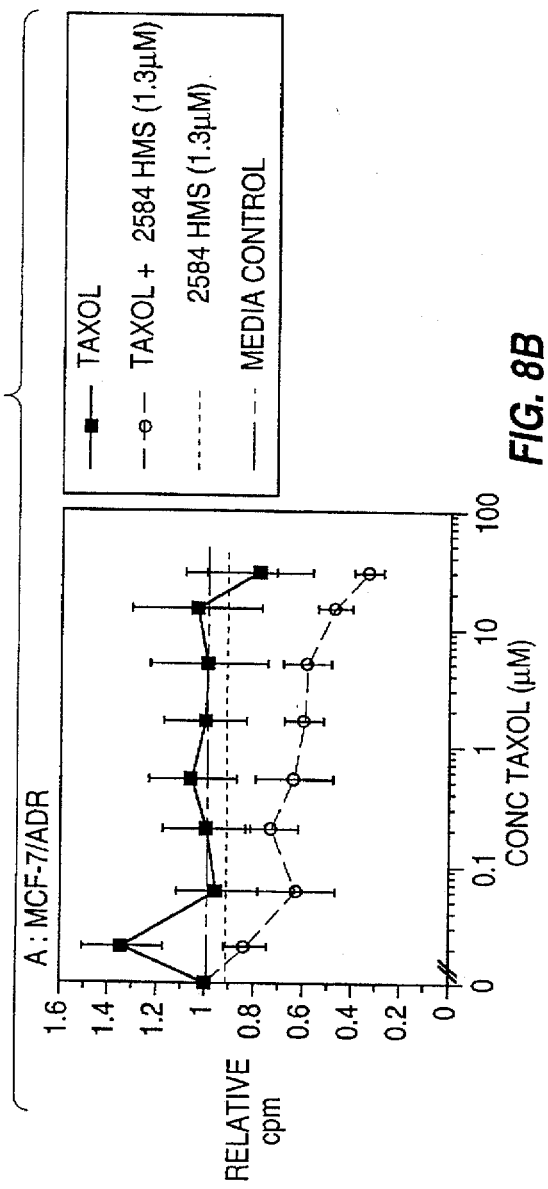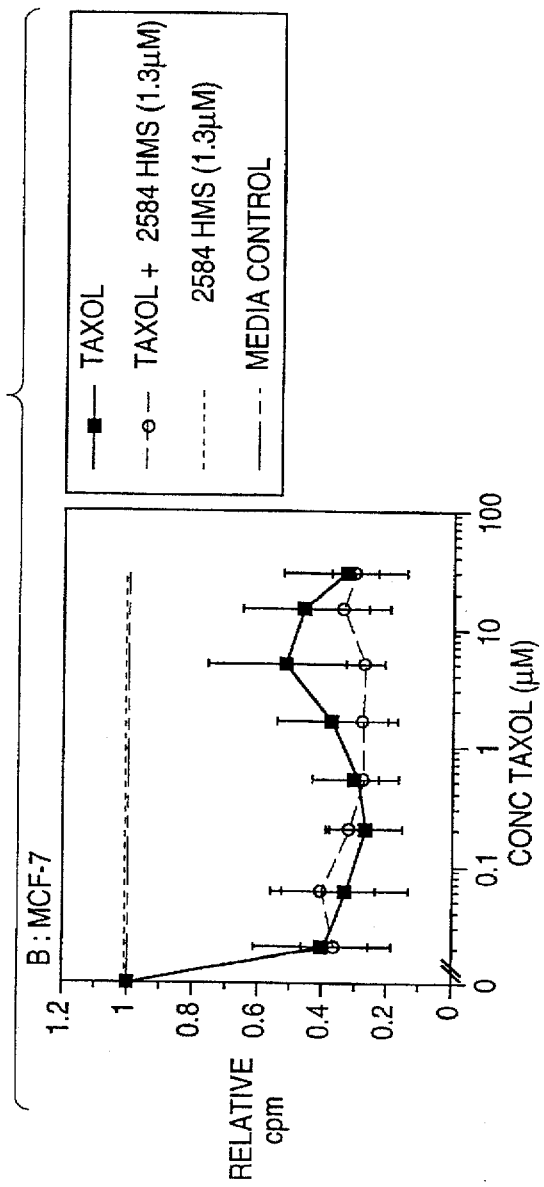

METHOD FOR REVERSING MULTIPLE DRUG RESISTANT PHENOTYPE

TECHNICAL FIELD OF THE INVENTION

The present invention provides a method for a reversal of the multiple drug resistant phenotype.

BACKGROUND OF THE INVENTION

Treatment of human malignancies with certain chemotherapeutic agents is frequently ineffective due to either endogenous or acquired tumor cell resistance. The problem is further exacerbated since many of the mechanisms of tumor cell resistance results in collateral resistance to a wide range of structurally unrelated chemotherapeutic drugs with different mechanisms of action. Multidrug resistance in cancer therapy is a significant problem, and appears to be the main impediment to increasing cure rates with current chemotherapeutic agents. In the seven major worldwide pharmaceutical marketplaces alone (U.S., Japan, Germany, Italy, France, Spain, UK), approximately 2.04 million new cases of cancer are reported annually (Krul, "Emerging Cancer Therapies", *Decision Resources, Inc.* pp. 79–94, 1994). Of these, only 5–10% will respond successfully to chemotherapy. Approximately 40–45%, or more than 800, 000 patients annually will develop multidrug resistance to the chemotherapeutic regimes. Thus the emergence of multidrug resistance is a major obstacle to successful cancer chemotherapy worldwide.

Several mechanisms can account for multidrug resistance (MDR) at a molecular and cellular level. Decreased drug uptake or increased drug efflux, altered redox potential, enhanced DNA repair, increased drug sequestration mechanisms or amplification of the drug-target protein are all postulated cellular mechanisms for expression of tumor cell drug resistance to various chemotherapeutic agents. One mechanism by which tumor cells acquire MDR is by over expression of a transmembrane glycoprotein called P-glycoprotein (Pgp) (Endicott et al., *Annu. Rev. Biochem.* 59:137, 1989; Gerlach et al., *Cancer Surv.* 5:25, 1986; Look et al., *N. Engl. J. Med.* 311:231, 1984; and Riordan et al., *Nature* 316:817, 1985). Pgp is thought to act by rapidly pumping hydrophobic chemotherapeutic agents out of the tumor cells, and thereby decreasing intracellular accumulation of certain chemotherapeutic agents below their cytostatic concentrations. This problem has been addressed in vitro by increasing the drug concentration. However, since cancer chemotherapeutic agents are already dosed at their maximally tolerated range in vivo, increasing the doses only leads to unacceptable toxicity's (Bellamy et al., *Cancer Invest.* 8,547, 1990; and Moscow et al., *Cancer Chemotherapy Biol. Response Modifiers Ann.* 81,844, 1990).

P-gylcoprotein is a 170 kD, ATP-dependent plasma membrane protein which is structurally similar to the cystic fibrosis transporter protein, the major histocompatibility complex-linked peptide transporter, and a non-P-glycoprotein-related multidrug resistance protein (MRP) (Rommens et al., *Proc. Natl. Acad. Sci. USA* 88:7500, 1991; Juranka et al., *FASEB J.* 3:2583, 1989; Cole et al. *Science* 258:1650, 1992; and Barrand et al., *J. Natl. Cancer Inst.* 86:110–117, 1994). P-glycoprotein is expressed in diverse sites including the normal human adrenal cortex, the luminal aspect of bile canaliculi and colonic epithelium, the renal tubular epithelium and the endothelial cell of the blood-brain and blood testicular barriers. The function of the P-glycoproteins at these sites is unclear but appears to function as an energy dependent pump of broad specificity possibly related to secretion of hormones and protection against toxins. Expression of the P-glycoprotein can actively efflux a large number of hydrophobic, and heterocyclic cancer chemotherapeutic agents including adriamycin (doxorubicin), colchicine, colcemid, etoposide, paclitaxel, vincristine, vinblastine as well as others.

P-glycoproteins are encoded by a highly conserved family of genes (Georges et al., *Proc. Natl. Acad. Sci. USA* 87:152, 1990). The mdr-1 gene encodes class I P-glycoprotein that confers multidrug resistance in humans (Ng et al., *Mol. Cell. Biol.* 9:1224, 1989; Van Der Bliek et al., *EMBO J.,* 6:3325, 1987). The mdr-2 and mdr-3 genes encode class III human P-glycoprotein, whose function is unclear (Arias et al., "Structure and function of P-glycoprotien and normal liver intestine" in *Xenobiotics and Cancer,* Ernster et al (eds.), Japan Sci. Soc. Press, Tokyo/Taylor and Francis, LTD., London, pp. 229–239, 1991). The pgp-1 and pgp-2 genes in hamsters and the mdr-3 and mdr-1 genes in mice encode the class I and II proteins, both of which confer multidrug resistance in rodents (Ng et al., *Mol. Cell Biol.* 9:1224, 1989; Van Der Bliek et al. *EMBO J.,* 6:3325, 1987; and Arias et al., "Structure and function of P-glycoprotien and normal liver intestine" in *Xenobiotics and Cancer,* L Ernster et al (eds.), Japan Sci. Soc. Press, Tokyo/Taylor and Francis, LTD., London, pp. 229–239, 1991).

Several lines of evidence support cause-effect association between increased P-glycoprotein and multidrug resistance in vitro. Structural features of the protein are characteristic of an energy-dependent efflux pump (Gros et al., *Cell* 47:371,1986). Over expression of the protein is associated with multidrug resistance (Gerlach et al., *Cancer Surv.* 5:25, 1986). Also, there is a positive correlation between the degree of expression of P-glycoprotein and a drug-resistant phenotype (Fojo et al., *Proc. Natl. Acad. Sci. USA,* 84:7735–7738, 1987). Transfection of drug-sensitive cells with full length cDNA for mdr-1 confers the multidrug resistant phenotype (Ueda et al., *Proc. Natl. Acad. Sci. USA* 84: 3004–3008, 1987). Also, point mutations in mdr-1 diminish expression of drug resistance (Choi et al., *Cell* 53:519, 1988).

Cancers of the colon, kidney, breast, adrenal cortex and liver frequently show high levels of P-glycoprotein at diagnosis, even though the patients have not been previously treated with anti cancer drugs (Gerlach et al., *Cancer Surv.* 5:25, 1986; Arias, *Hepatology* 12:159–165, 1990). In a variety of tumor types, relapse or disease progression following the initial chemotherapy regime is refractory to treatment, and frequently involves MDR and expression of elevated levels of mdr-1 (Gerlach et al., *Cancer Surv.* 5:25, 1986; and *Clin. Cancer Res.* 1:81, 1994). In fact, over expression of P-glycoprotein was initially described in cell lines exposed to stepwise increasing concentrations of various cancer chemotherapeutic agents (Endicott et al., *Annu. Rev. Biochem.* 59:137, 1989). Drug resistance can manifest in cells with low gene copy number and can be due to regulation at the transcrptional, translational or post-translational level. Although in vitro studies often show amplification of mdr-1 as the cause for drug resistance, (Juranka et al., *FASEB J.* 3:2583, 1989; McClean et al., *Proc. Am, Assoc. Cancer Res.* 34:313, 1993), elevated gene copy number is apparently rare in human tumors (Chabner et al., *J. Natl. Cancer Inst.* 81:910, 1989).

Increased levels of mdr-1 gene product or its mRNA have been associated with poor prognosis in a number of human tumor studies. Clinical studies in breast carcinoma (Ro et al., *Hum. Pathol.* 21:737, 1990; and Verelle et al., *J. Natl. Cancer Inst.* 83:111, 1991) have shown that a significant percentage of patients expressed large levels of P-glycoprotein and the low P-glycoprotein expressing patients had significantly better rates of response to chemotherapy and progression-free survival than did high expressing groups. Sixty-eight percent of the tumors in a retrospective study of colon carcinoma expressed high levels of P-glycoprotein and over expression correlated with aggressiveness measured by blood cell invasion and metastasis (Weinstein et al., *Hum. Pathol.* 21:34, 1990). In three clinical studies involving acute myelogenous leukemia, the mdr-1 negative groups all had higher rates of complete remission and longer durations of disease-free survival than the mdr-1 positive groups (Parker et al., *J. Natl. Cancer Inst.* 83:708, 1991; Marie et al., *Blood* 78:589, 1991; and Campos et al., *Blood* 79:473, 1992). In three studies in neuroblastoma, investigators have shown that mdr-1 expression frequently occurs in non localized and post treatment tumors and correlates with poor prognosis (Chan et al., *N. Eng. J. Med.* 325:1608, 1991; Bourhis et al., *J. Natl. Cancer Inst.* 81:1401, 1989; and Goldstein et al., *J. Clin. Oncol.* 8:128,1990). Likewise in rhabdomyosarcoma, P-glycoprotein levels were correlated with increased malignant staging and the P-glycoprotein negative group had significantly better rate of response as well as longer durations of relapse-free survival and overall survival than did the P-glycoprotein positive patients (Chan et al., *J. Clin Oncol.* 8:689, 1990). P-glycoprotein expression was also highly correlated with advanced and refractory myeloma (Epstein et al., *Blood* 74:913–917, 1989) Together these data suggest that there is a correlation of P-glycoprotein expression with clinical prognosis in a variety of human malignancies.

Drugs that are alleged to reverse MDR have been shown to have mechanisms by decreasing drug efflux (e.g., calcium channel blockers verapramil, diltiazem and nicardipidine (Tsuro et al., *Cancer Res.* 43:2905, 1983), calmodulin inhibitors reserpine, quinidine or quineine (Kanamaru et al., *J. Natl. Cancer Inst.* 81:844, 1989), cyclosporin A (Twentyman et al., *Br. J. Cancer* 56:55,1987), cyclosporin derivatives (Boesch et al., *Exp. Cell Res.* 196:26–32, 1991), or FK506 and rapamycin (Arceci et al., *Blood* 80:1528–1536, 1992)). Clinical reversal of resistance for most of these agents has been limited, mainly due to clinically toxic concentration levels that were needed to achieve a reversal of resistance.

Therefore, there is a need in the art to find more effective MDR reversing agents that have additional beneficial effects to cancer patients, such as tumor-specific cytotoxicity, inhibition of angiogenesis and lack of significant side effects. The present invention was made when it was discovered that a group of compounds that were directly cytotoxic to tumor cells, could also reverse the MDR phenotype and extremely low concentrations and render resistant tumor cells sensitive to other chemotherapeutic agents.

SUMMARY OF THE INVENTION

The present invention provides a method for reversing the MDR phenotype in tumors insensitive to hydophobic chemotherapeutic drugs due to over expression of mdr-1, comprising administering an effective amount of a long-chain amino alcohol compound. The present invention further provides a method for preventing the development of MDR during cancer chemotherapy treatments, comprising administering during cancer chemotherapy treatments an effective amount of a long-chain amino alcohol compound. The long chain amino alcohol compounds include resolved enantiomers and/or diastereomers, hydrates, salts, solvates and mixtures thereof, the long chain amino alcohol compounds having a straight or branched aliphatic hydrocarbon structure of formula I:

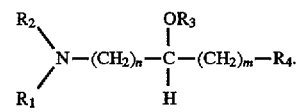

In formula I, n is an integer from one to four and m is an integer from four to twenty. Independently, $R_1$ and $R_2$ are hydrogen, a straight or branched chain alkyl, alkenyl or alkynyl of up to twenty carbon atoms in length or —$(CH_2)_w R_5$. If $R_1$ or $R_2$ is —$(CH_2)_w R_5$, w may be an integer from one to twenty and $R_5$ may be an hydroxyl, halo, $C_{1-8}$ alkoxyl group or a substituted or unsubstituted carbocycle or heterocycle. Alternatively, $R_1$ and $R_2$ may jointly form a substituted or unsubstituted, saturated or unsaturated heterocycle having from four to eight carbon atoms, N being a hetero atom of the resulting heterocycle. $R_3$ may be either hydrogen or $C_{1-3}$. Preferred long chain amino alcohol compounds may have one of $R_1$ or $R_2$ and $R_3$ that form a substituted or unsubstituted linking carbon chain, having from one to four carbon atoms. This $R_1/R_3$ or $R_2/R_3$ linking chain will join the O and N in a cyclic structure, an integer sum equal to n+ a number of carbon atoms in the linking carbon chain being less than six.

In the long chain amino alcohol compounds, a total sum of carbon atoms comprising $R_1$ or $R_2$, $(CH_2)_n$ and $(CH_2)_m$ does not exceed forty. $R_4$ is a terminal moiety comprising a substituted or unsubstituted, oxidized or reduced ring system, the ring system having a single ring or two to three fused rings, a ring comprising from three to seven ring atoms. However, if $R_4$ is phthalimide, m of formula I is not less than five.

The long chain amino alcohol compounds may include resolved enantiomers and/or diastereomers, hydrates, salts, solvates and mixtures thereof that have a straight or branched aliphatic hydrocarbon structure of formula II:

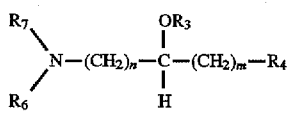

In the above formula II, n, m, $R_3$, and $R_4$ are defined as provided in formula I above. $R_6$ and $R_7$ are hydrogen, a straight or branched chain alkane, alkene or alkyne of up to twenty carbon atoms in length, or —$(CH_2)_xR_8$, at least one of $R_6$ or $R_7$ being —$(CH_2)_xR_8$. In formula II, x is an integer from zero to fourteen and $R_8$ is a moiety having a general structure as provided in formula III

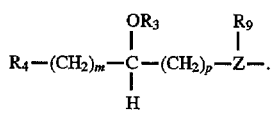

In formula III above, m, $R_3$, and $R_4$ are defined as provided in formula I above. Z is N or CH and p is an integer from zero to four. $R_9$ is H or a straight or branched chain alkane, alkene or alkyne of up to twenty carbon atoms in length.

BRIEF DESCRIPTION OF THE DRAWINGS

FIG. 1 shows that preincbation with CT-2584 reverses inherent doxorubicin resistance of P388/MDR. The parent cell line, P388, was not sensitized significantly by preincubation with CT-2584.

FIGS. 4–6 show that a cytotoxic enhancement by CT-2584 can take place with other agents which are transported by the P-glycoprotein membrane pump. Specifically, FIG. 4 shows that LZ100 cells were sensitized to paclitaxel (Taxol®) by preincubation with CT-2584 (1.3 μM). FIG. 5 shows that LZ100 cells were sensitized to colchicine, with only small enhancement with the parental, non pgp-1 amplified, V-79 cells. FIG. 6 shows that LZ100 cells were sensitized to actinomycin D, with only small enhancement with the parental, non pgp-1 amplified, V-79 cells.

FIG. 7 shows that MCF-7/ADR cells were also sensitized to doxorubicin by preincubation with CT-2584 (1.3 μM). MCF-7 cells are a sensitive and non-amplified or over expressing parental line and MCR cells were not sensitized to doxorubicin by preincubation with CT-2584 (1.3 μM).

FIG. 8 shows that MCF-7/ADR cells were sensitized to Taxol by preincubation with CT-2584 (1.3 μM).

DETAILED DESCRIPTION OF THE INVENTION

Figure 1:
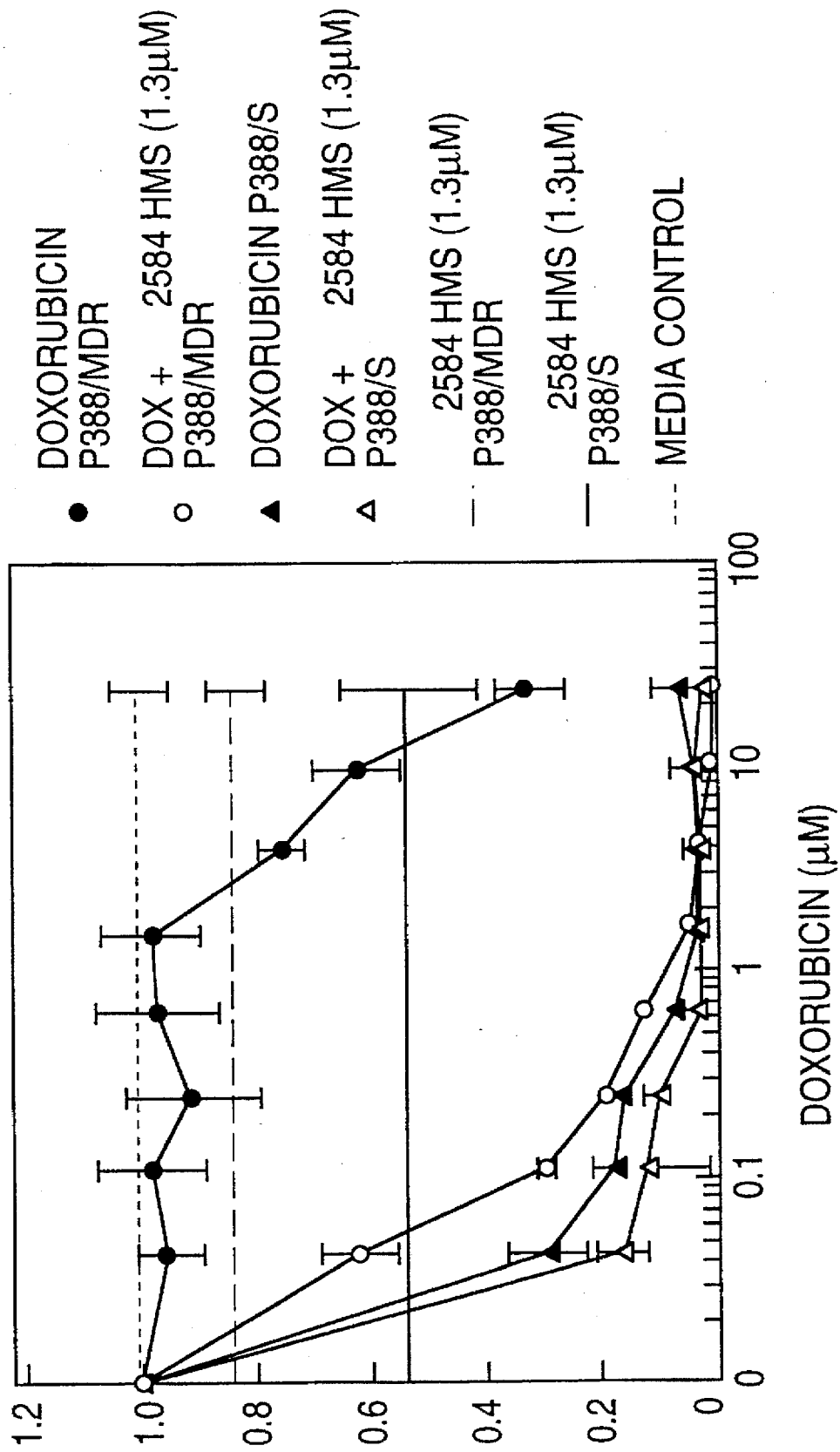
FIG. 1 shows cytotoxic sensitization of P388/MDR cells by preincubation with a subcytotoxic concentration of CT-2584 (1.3 μM) (1-(11-Dodecylamino-10-hydroxyundecyl)-3,7-dmethylxanthine).

The present invention provides a method for reversing multiple drug resistant (MDR) phenotype in tumors insensitive to hydrophobic chemotherapeutic drugs due to over expression of mdr-1, comprising administering an effective amount of a long-chain amino alcohol compound. The present invention further provides a method for preventing the development of MDR during cancer chemotherapy treatments, comprising administering during cancer chemotherapy treatments an effective amount of a long-chain amino alcohol compound. Hydrophobic chemotherapeutic drugs include, for example, paclitaxel (Taxol®) and related inhibitors of tubulin depolymerization, mitomycin, actinomycin and related antitumor antibiotics (e.g., actinomycin D and azetomycin II, and mithramycin), vinblastine and other vinca alkaloids (e.g., vincristine, vindesine, and VM-26), doxorubicin and related anthracycline antibiotics, nitidine, coralyne, hycanthone AMSA, ellipticine, chartreusin, etoposide, mayatansine, oncodazole, and a number of inhibitors of protein biosynthesis as described in Johnson et al., Cancer Treatment Reports 62:1535–1547, 1978.

Preferably, the long chain amino alcohol compound is CT-2584 (1-(11-Dodecylamino-10-hydroxytmdecyl)-3,7-dmethylxanthine ).

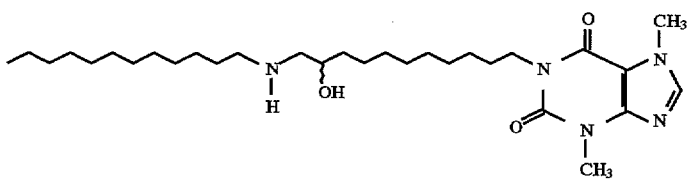

The long chain amino alcohol compounds include, for example, resolved enantiomers and/or diastereomers, hydrates, salts, solvates and mixtures thereof, the compound having a straight or branched aliphatic hydrocarbon structure of formula I:

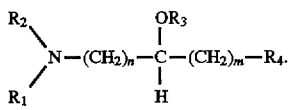

In formula I, n is an integer from one to four and m is an integer from four to twenty. Independently, $R_1$ and $R_2$ are hydrogen, a straight or branched chain alkyl, alkenyl or alkynyl of up to twenty carbon atoms in length or —$(CH_2)_w R_5$. If $R_1$ or $R_2$ is —$(CH_2)_w R_5$, w may be an integer from one to twenty and $R_5$ may be an hydroxyl, halo, $C_{1-8}$ alkoxyl group or a substituted or unsubstituted carbocycle or heterocycle. Alternatively, $R_1$ and $R_2$ may jointly form a substituted or unsubstituted, saturated or unsaturated heterocycle having from four to eight carbon atoms, N being a hetero atom of the resulting heterocyle. $R_3$ may be either hydrogen or $C_{1-3}$. Preferred compounds may have one of $R_1$ or $R_2$ and $R_3$ that form a substituted or unsubstituted linking carbon chain, having from one to four carbon atoms. This $R_1/R_3$ or $R_2/R_3$ linking chain will join the O and N in a cyclic structure, an integer sum equal to n+ a number of carbon atoms in the linking carbon chain being less than six.

In the compounds, a total sum of carbon atoms comprising $R_1$ or $R_2$, $(CH_2)_n$ and $(CH_2)_m$ does not exceed forty. $R_4$ is a terminal moiety comprising a substituted or unsubstituted, oxidized or reduced ring system, the ring system having a single ring or two to three fused rings, a ring comprising from three to seven ring atoms. However, if $R_4$ is phthalimide, m of formula I is not less than five.

In preferred compounds of the invention which have a general structure of formula I, $R_5$ may be hydroxy, chloro, fluoro, bromo, or $C_{1-6}$ alkoxy, or a substituted or unsubstituted, saturated or unsaturated heterocycle having from four to seven carbon atoms, more preferably, a mono-, di- or tri-substituted carbocycle or heterocycle. In the compounds, $(CH_2)_m$ may be unsubstituted, or more preferably, $(CH_2)_m$ is substituted by a halogen atom, an hydroxyl group, or substituted or unsubstituted $C_{(1-10)}$ alkoxyl, $C_{(1-10)}$ alkyl, $C_{(2-10)}$ alkenyl or $C_{(1-10)}$ alkynyl group. Substituents of the $R_1/R_3$ or $R_2/R_3$ linking chain may include, without limitation, a $C_{(1-4)}$ alkyl, $C_{(2-4)}$ alkenyl, hydroxyl, carbonyl, amino, thio, thiol, thiocarbonyl and imino group or a single atom, such as, for example, chlorine, bromine, fluorine and oxygen In the compounds comprising a non-cyclic, terminal moiety, the terminal moiety may include, without limitation, an acetamidyl, amidyl, aminyl, amino acid (one or two), carbonyl, carboxyl, alkoxylcarbonyl, halo, hydro, hydroxyl, glutaric acid, alkoxyl, phosphatyl, phosphonatyl, sulfatyl, sulfonatyl, sulfonyl, sulfoxidyl, thio or thiolalkoxylcarbonyl group or a simple ionic functional group. In more preferred compounds, the terminal moiety ring system may be saturated, but alternatively, preferred compounds have a ring system terminal moiety having at least one unsaturated carbon-carbon double bond. In more preferred compounds of the invention, ring system substituents may include, but are not intended to be limited to, $C_{(1-4)}$ alkyl, $C_{(2-4)}$ alkenyl, hydroxyl, carbonyl, amino, thio, thiol, thiocarbonyl and imino group or a single atom. Single atoms corresponding to ring substituents may include, but are not intended to be limited to, chlorine, bromine, fluorine and oxygen.

The compounds may have ring systems, in which all ring atoms are carbon atoms. Preferred compounds, in which all ring atoms are carbon atoms, may have ring systems that include, but are not intended to be limited to, one of the following groups: phenyl, cyclopropyl, cyclobutyl, cyclopentyl, cyclopentenyl, cyclohexyl, cyclohexenyl, cycloheptyl, cycloheptenyl, biscyclooctyl, indanyl, indenyl, decalinyl, resorcinolyl, tetralinyl, α-tetralonyl, 1-indanonyl, cyclohexanedionyl or cyclopentanedionyl.

In more preferred compounds of the invention, at least one ring atom of the ring system may be other than carbon. For preferred compounds that have a ring system terminal moiety, having at least one ring atom which is other than carbon, then the total number of non-carbon ring atoms should not exceed a value "X," specified by the equation: X=total number of ring atoms−1. Non-carbon ring atoms may include, for example, atoms such as nitrogen, oxygen, sulfur and phosphorus.

Terminal moiety ring systems which have at least one ring atom that is other than carbon may include, for example, ring systems that have three or four atoms in at least one ring of the system. Preferred ring systems having at least one non-carbon atom and at least one ring which has three or four atoms may include, but are not intended to be limited to: azetidinedionyl; azetidinonyl; azetidinyl; aziridinonyl; aziridinyl; azirinyl; diaziridinonyl; diaziridinyl; diazirinyl; dioxetanyl; dioxiranyl; dithietanyl; episulfonyl; lactamyl; lactonyl; oxathietanyl; oxathiiranyl; oxaziranyl; oxaziridinyl; oxetananonyl; oxetanonyl; oxetanyl; oxiranyl; sultamyl; sultinyl; sultonyl; thiazetidinyl; thiaziridinyl; thietanyl or thiiranyl.

Alternatively, preferred compounds may have terminal moieties that have at least one ring having at least five ring atoms, at least one of the at least five ring atoms being other than carbon. In these preferred compounds, the at least five-atom ring system may include, but is not intended to be limited to, one of the following substituted or unsubstituted groups: adeninyl; alloxanyl; alloxazinyl; anthracenyl; anthrenyl; azapinyl; azapurinyl; azinyl; azolyl; barbituric acid; biotinyl; chromylenyl; cinnolinyl; coumarinyl; coumaronyl; depsidinyl; diazepinyl; diazinyl; diazocinyl; dioxadiazinyl; dioxanyl; dioxenyl; dioxepinyl; dioxinonyl; dioxolanyl; dioxolonyl; dioxolyl; dioxanthylenyl; enantholactamyl; flavanyl; flavinyl; flavonyl; fluoranyl; fluorescienyl; furandionyl; furanochromanyl; furanonyl; furanyl; furazanyl; furoxanyl; guaninyl; hydroquinolinyl; imidazolethionyl; imidazolinyl; imidazolonyl; imidazolyl; indolizidinyl; indolizinyl; indolonyl; indolyl; isatinyl; isatogenyl; isoindolinyl; isoquinolinyl; isothiazolyl; isoxazolyl; lactamyl; lactonyl; lumazinyl; naphthacenyl; naphthalenyl; oroticyl; oxadiazinyl; oxadiazolyl; oxathianyl; oxathiazinonyl; oxathiolanyl; oxatriazolyl; oxazinonyl; oxazolidinonyl; oxazolidinyl; oxazolinonyl; oxazolinyl; oxazolonyl; oxazolyl; oxolenyl; pentazinyl; pentazolyl; petrazinyl; phthalimidyl; phthalonyl; piperazindionyl; piperazinodionyl; piperazinyl; piperidinyl; piperidonyl; prolinyl; prylenyl; pteridinyl; pterinyl; purinyl; pyradinyl; pyranoazinyl; pyranoazolyl; pyranonyl; pyranyl; pyrazinyl; pyrazolidinyl; pyrazolidonyl; pyrazolinonyl; pyrazolinyl; pyrazolonyl;

pyrazolyl; pyrenyl; pyridazinyl; pyridazonyl; pyridinyl; pyrimidinyl; pyrimidionyl; pyronyl; pyrrolidinyl; pyrrolyl; quinazolidinyl; quinazolinonyl; quinazolinyl; quinolinyl; quinolizinyl; quinonyl; quinoxalinyl; quinuclidinyl; rhodaminyl; spirocoumaranyl; succinimidyl; sulfolanyl; sulfolenyl; sultamyl; sultinyl; sultonyl; sydononyl; tetraoxanyl; tetrazepinyl; tetrazinyl; tetrazolyl; tetronyl; thiazepinyl; thiazinyl; thiazolyl; thiepinyl; thiolanyl; thiolenyl; thiolyl; thiophenyl; thyminyl; triazepinonyl; triazepinyl; triazinyl; triazolinyl; triazolyl; trioxanyl; trithianyl; trixolanyl; trizinyl; tropanyl; uracilyl; xanthenyl; xanthinyl; xanthonyl; xanthydrolyl or xylitolyl.

For compounds having a preferred ring system terminal moiety having at least one ring with one hetero atom, a ring system may include one of the following: acridinyl; acridonyl; alkylpyridinyl; anthraquinonyl; ascorbyl; azaazulenyl; azabenzanthracenyl; azabenzanthrenyl; azabenzophenanthrenyl; azachrysenyl; azacyclazinyl; azaindolyl; azanaphthacenyl; azanaphthalenyl; azapyrenyl; azatriphenylenyl; azepinyl; azinoindolyl; azinopyrrolyl; benzacridinyl; benzazapinyl; benzofuryl; benzonaphthyridinyl; benzopyranonyl; benzopyranyl; benzopyronyl; benzoquinolinyl; benzoquinolizinyl; benzothiepinyl; benzothiophenyl; benzylisoquinolinyl; biotinyl; bipyridinyl; butenolidyl; butyrolactonyl; caprolactamyl; carbazolyl; carbolinyl; catechinyl; chromenopyronyl; chromonopyranyl; coumarinyl; coumaronyl; decahydroquinolinyl; decahydroquinolonyl; diazaanthracenyl; diazaphenanthrenyl; dibenzazepinyl; dibenzofuranyl; dibenzothiophenyl; dichromylenyl; dihydrofuranyl; dihydroisocoumarinyl; dihydroisoquinolinyl; dihydropyranyl; dihydropyridinyl; dihydropyridonyl; dihydropyronyl; dihydrothiopyranyl; diprylenyl; dioxanthylenyl; enantholactamyl; flavanyl; flavonyl; fluoranyl; fluorescienyl; furandionyl; furanochromanyl; furanonyl; furanoquinolinyl; furanyl; furopyranyl; furopyronyl; heteroazulenyl; hexahydropyrazinoisoquinolinyl; hydrofuranyl; hydrofurnanonyl; hydroindolyl; hydropyranyl; hydropyridinyl; hydropyrrolyl; hydroquinolinyl; hydrothiochromenyl; hydrothiophenyl; indolizidinyl; indolizinyl; indolonyl; isatinyl; isatogenyl; isobenzofurandionyl; isobenzofuranyl; isochromanyl; isoflavonyl; isoindolinyl; isoindolobenzazepinyl; isoindolyl; isoquinolinyl; isoquinuclidinyl; lactamyl; lactonyl; maleimidyl; monoazabenzonaphthenyl; naphthalenyl; naphthimidazopyridinedionyl; naphthindolizinedionyl; naphthodihydropyranyl; naphthofuranyl; naphthothiophenyl; naphthyridinyl; oxepinyl; oxindolyl; oxolenyl; perhydroazolopyridinyl; perhydroindolyl; phenanthraquinonyl; phenanthridinyl; phenanthrolinyl; phthalideisoquinolinyl; phthalimidyl; phthalonyl; piperidinyl; piperidonyl; prolinyl; pyradinyl; pyranoazinyl; pyranoazolyl; pyranopyrandionyl; pyranopyridinyl; pyranoquinolinyl; pyranopyradinyl; pyranyl; pyrazolopyridinyl; pyridinethionyl; pyridinonaphthalenyl; pyridinopyridinyl; pyridinyl; pyridocolinyl; pyridoindolyl; pyridopyridinyl; pyridopyrimidinyl; pyridopyrrolyl; pyridoquinolinyl; pyronyl; pyrrocolinyl; pyrrolidinyl; pyrrolizidinyl; pyrrolizinyl; pyrrolodiazinyl; pyrrolonyl; pyrrolopyrimidinyl; pyrroloquinolonyl; pyrrolyl; quinacridonyl; quinolinyl; quinolizidinyl; quinolizinyl; quinolonyl; quinuclidinyl; rhodaminyl; spirocoumaranyl; succinimidyl; sulfolanyl; sulfolenyl; tetrahydrofuranyl; tetrahydroisoquinolinyl; tetahydropyranyl; tetrahydropyridinyl; tetrahydrothiapyranyl; tetrahydrothiophenyl; tetrahydrothiopyranonyl; tetrahydrothiopyranyl; tetronyl; thiabenzenyl; thiachromanyl; thiadecalinyl; thianaphthenyl; thiapyranyl; thiapyronyl; thiazolopyridinyl; thienopryidinyl; thienopyrrolyl; thienothiophenyl; thiepinyl; thiochromenyl; thiocoumarinyl; thiophenyl; thiopyranyl; triazaanthracenyl; triazinoindolyl; triazolopyridinyl; tropanyl; xanthenyl; xanthonyl or xanthydrolyl.

In addition, long chain amino alcohol compounds that have a preferred ring system terminal moiety having at least one ring with two hetero atoms, the ring system may include: adeninyl; alloxanyl; alloxazinyl; anthranilyl; azabenzanthrenyl; azabenzonaphthenyl; azanaphthacenyl; azaphenoxazinyl; azapurinyl; azinyl; azoloazinyl; azolyl; barbituric acid; benzazinyl; benzimidazolethionyl; benzimidazolonyl; benzimidazolyl; benzisothiazolyl; benzisoxazolyl; benzocirmolinyl; benzodiazocinyl; benzodioxanyl; benzodioxolanyl; benzodioxolyl; benzopyridazinyl; benzothiazepinyl; benzothiazinyl; benzothiazolyl; benzoxazinyl; benzoxazolinonyl; benzoxazolyl; cinnolinyl; depsidinyl; diazaphenanthrenyl; diazepinyl; diazinyl; dibenzoxazepinyl; dihydrobenzimidazolyl; dihydrobenzothiazinyl; dihydrooxazolyl; dihydropyridazinyl; dihydropyrimidinyl; dihydrothiazinyl; dioxanyl; dioxenyl; dioxepinyl; dioxinonyl; dioxolanyl; dioxolonyl; dioxopiperazinyl; dipyrimidopyrazinyl; dithiolanyl; dithiolenyl; dithiolyl; flavinyl; furopyrimidinyl; glycocyamidinyl; guaninyl; hexahydropyrazinoisoquinolinyl; hexahydropyridazinyl; hydantoinyl; hydroimidazolyl; hydropyrazinyl; hydropyrazolyl; hydropyridazinyl; hydropyrimidinyl; imidazolinyl; imidazolyl; imidazoquinazolinyl; imidazothiazolyl; indazolebenzopyrazolyl; indoxazenyl; inosinyl; isoalloxazinyl; isothiazolyl; isoxazolidinyl; isoxazolinonyl; isoxazolinyl; isoxazolonyl; isoxazolyl; lumazinyl; methylthyminyl; methyluracilyl; morpholinyl; naphthimidazolyl; oroticyl; oxathianyl; oxathiolanyl; oxazinonyl; oxazolidinonyl; oxazolidinyl; oxazolidonyl; oxazolinonyl; oxazolinyl; oxazolonyl; oxazolopyrimidinyl; oxazolyl; perhydrocinnolinyl; perhydropyrroloazinyl; perhydropyrrolooxazinyl; perhydropyrrolothiazinyl; perhydrothiazinonyl; perimidinyl; phenazinyl; phenothiazinyl; phenoxathiinyl; phenoxazinyl; phenoxazonyl; phthalazinyl; piperazindionyl; piperazinodionyl; polyquinoxalinyl; pteridinyl; pterinyl; purinyl; pyrazinyl; pyrazolidinyl; pyrazolidonyl; pyrazolinonyl; pyrazolinyl; pyrazolobenzodiazepinyl; pyrazolonyl; pyrazolopyridinyl; pyrazolopyrimidinyl; pyrazolotriazinyl; pyrazolyl; pyridazinyl; pyridazonyl; pyridopyrazinyl; pyridopyrimidinyl; pyrimidinethionyl; pyrimidinyl; pyrimidionyl; pyrimidoazepinyl; pyrimidopteridinyl; pyrrolobenzodiazepinyl; pyrrolodiazinyl; pyrrolopydmidinyl; quinazolidinyl; quinazolinonyl; quinazolinyl; quinoxalinyl; sultamyl; sultinyl; sultonyl; tetrahydrooxazolyl; tetrahydropyrazinyl; tetrahydropyridazinyl; tetrahydroquinoxalinyl; tetrahydrothiazolyl; thiazepinyl; thiazinyl; thiazolidinonyl; thiazolidinyl; thiazolinonyl; thiazolinyl; thiazolobenzimidazolyl; thiazolyl; thienopyrimidinyl; thiazolidinonyl; thyminyl; triazolopyrimidinyl; uracilyl; xanthinyl; or xylitolyl.

Terminal ring systems having at least one ring having three hetero atoms may include, but are not intended to be limited to, one of the following ring systems: azabenzonaphthenyl; benzofuroxanyl; benzothiadiazinyl; benzotriazepinonyl; benzotriazolyl; benzoxadizinyl; dioxadiazinyl; dithiadazolyl; dithiazolyl; furazanyl; furoxanyl; hydrotriazolyl; hydroxytrizinyl; oxadiazinyl; oxadiazolyl; oxathiazinonyl; oxatriazolyl; pentazinyl; pentazolyl; petrazinyl; polyoxadiazolyl; sydononyl; tetraoxanyl; tetrazepinyl; tetrazinyl; tetrazolyl; thiadiazinyl; thiadiazolinyl; thiadiazolyl; thiadioxazinyl; thiatdazinyl; thiatriazolyl; thiatriazolyl; triazepinyl; triazinoindolyl; triazinyl; triazolinedionyl; triazolinyl; triazolyl; trioxanyl; triphenodioxazinyl; triphenodithiazinyl; trithiadiazepinyl; trithianyl; or trixolanyl.

In these long chain amino alcohol compounds, the most preferred ring systems include, for example, dimethylxanthinyl, methylxanthinyl, phthalimidyl, homophthalimidyl, methylbenzoyleneureayl, quinazolinonyl, octylcarboxamidobenzenyl, methylbenzamidyl, methyldioxotetrahydropteridinyl, glutarimidyl, piperidonyl, succinimidyl, dimethoxybenzenyl, methyldihydrouracilyl, methyluracilyl, methylthyminyl, piperidinyl, dihydroxybenzenyl, or methylpurinyl, even more preferably, methylxanthinyl, dimethylxanthinyl or a derivative thereof. The most preferred compounds may also have a ring-system terminal moiety that has at least one substituent bonded to at least one ring of the ring system, the at least one substituent being bonded to a carbon ring atom of the at least one ring by an sp bond, in which the carbon ring atom is adjacent to a hetero atom of the ring. Also, in the most preferred embodiments of the compounds, ring-system terminal moieties, having at least one hetero atom, may be linked to $(CH_2)_m$ of formula I by a bond between the at least one hetero atom and $—(CH_2)_m$.

The compounds may include resolved enantiomers and/or diastereomers, hydrates, salts, solvates and mixtures thereof of compounds that have a straight or branched aliphatic hydrocarbon structure of formula II:

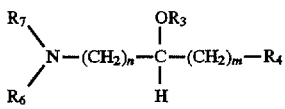

In the above formula II, n, m, $R_3$, and $R_4$ are defined as provided in formula I above. $R_6$ and $R_7$ are hydrogen, a straight or branched chain alkane, alkene or alkyne of up to twenty carbon atoms in length, or $—(CH_2)_xR_8$, at least one of $R_6$ or $R_7$ being $—(CH_2)_xR_8$. In formula II, x is an integer from zero to fourteen and $R_8$ is a moiety having a general structure as provided in formula III

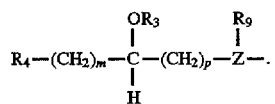

In formula III above, m, $R_3$, and $R_4$ are defined as provided in formula I above. Z is N or CH and p is an integer from zero to four. $R_9$ is H or a straight or branched chain alkane, alkene or alkyne of up to twenty carbon atoms in length.

Preferred long chain amino alcohol compounds include, but are not intended to be limited to, both R and S enantiomers and racemic mixtures of the following compounds:
N-(9-Octylamino-8-hydroxynonyl)-phthalimide
N-(11-Octylamino-10-hydroxyundecyl)-homophthalimide
1-(5-hydroxy-6-(N-benzyl)aminohexyl)-3-methylbenzoyleneurea
3-(11,10-Oxidoundecyl)-quinazoline4(3H)-one
$N^2$-(5-hydroxy-6-($N^3$-propyl)-aminohexyl)-($N^1$-propyl)-glutaric acid
2-(11-Octylamino-10-hydroxyundecylcarboxamido)-octylcarboxamidobenzyl
1-Octylamino-2,11-undecadiol
1-(9-Octylamino-8-hydroxynonyl)-3-methylxanthine
1-(9-Tetradecylamino-8-hydroxynonyl)-3-methylxanthine
1-(11-Octylamino-10-hydroxyundecyl)-3-methylxanthine
7-(11-Octylamino-10-hydroxyundecyl)-1,3-dimethylxanthine
1-(11,10-Octylamino-10-hydroxyundecyl)-1-methyl-2,4-dioxotetrahydropteridine
1-(5-hydroxy-6-(N-benzyl) aminohexyl)-3,7-dimethylxanthine
1-(5-hydroxy-6-(N-propyl)aminohexyl)-3,7-dimethylxanthine
N-(11-Ocytlamino-10-hydroxyundecyl)-glutarimide
N-(11-Octylamino-10-hydroxyundecyl)-2-piperidone
N-(11-Octylamino-10-hydroxyundecyl)-succinimide
2-(11-Octylamino-10-hydroxytmdecyl)-1,3-dimethoxybenzene
3-(5-hydroxy-6-(N-propyl) aminohexyl)-1-methyluracil
3-(9 -Octylamino-8-hydroxynonyl)-1-methyluracil
3-(11-Octylamino-10-hydroxyundecyl)-1-methyluracil
3-(11-Octylamino-10-hydroxyundecyl)-1-methyldihydrouracil
3-(9-Octylamino-8-hydroxynonyl)-1-methylthymine
3-(5-hydroxy-6-(N-undecyl)aminohexyl)-1-methylthymine
3-(11-Octylamino-10-hydroxyundecyl)-1-methylthymine
3-(6-Propylamino-5-hydroxyhexyl)-1-methylthymine
1-(8-hydroxy-9-(N-benzyl)aminononyl)-3,7-dimethylxanthine
1-(5-hydroxy-6-(N-octyl) aminohexyl)-3,7-dimethylxanthine
1-(5-hydroxy-6-(N-(4-phenyl)butyl)aminohexyl)-3,7-dimethylxanthine
1-(6-Undecylamino-5-hydroxyhexyl)-3,7-dimethylxanthine
1-(5-hydroxy-6-(N-cyclohexylmethyl)aminohexyl)-3,7-dimethylxanthine
1-(5-hydroxy-6-(N-(6-hydroxy)hexyl)aminohexyl)-3,7-dimethylxanthine
1-(5-hydroxy-6-(N,N-dihexyl)aminohexyl)-3,7-dimethylxanthine
1-(5-hydroxy-6-(N-(4-methoxy)benzyl)aminohexyl)-3,7-dimethylxanthine
1-(8-hydroxy-9-(N-octyl)aminononyl)-3,7-dimethylxanthine
1-(5-hydroxy-6-(N-tetradecyl)aminohexyl)-3,7-dimethylxanthine
1-[6-(Cyclopropylmethylamino)-5-hydroxyhexyl)]-3,7-dimethylxanthine
1-(6-Decylamino-5-hydroxyhexyl)-3,7-dimethylxanthine
1-(6-Dodecylamino-5-hydroxyhexyl)-3,7-dimethylxanthine
1-(11-Benzylamino-10-hydroxyundecyl-3,7-dimethylxanthine
1-(9-Decylamino-8-hydroxynonyl)-3,7 -dimethylxanthine
1-(9-Dodecylamino-8-hydrononyl)-3,7-dimethylxanthine
1-(9-Tetradecylamino-8-hydroxynonyl)-3,7-dimethylxanthine
1-(11-Hexylamino-10-hydroxyundecyl)-3,7-dimethylxanthine
1-(11-Octylamino-10-hydroxyundecyl-3,7-dimethylxanthine
1-(6-Allylamino-5-hydroxyhexyl)-3,7-dimethylxanthine
1-(11-Allylamino-10-hydroxytmdecyl)-3,7-dimethylxanthine 1-(6-N-Methyloctadecylamino-5-hydroxyhexyl)-3,7-dimethylxanthine
1-(11-Decylamino-10-hydroxyundecyl)-3,7-dimethylxanthine
1-(11-Dodecylamino-10-hydroxyundecyl)-3,7-dmethylxanthine
1-(11-Tetradecylamino-10-hydroxyundecyl)-3,7-dimethylxanthine
1-[11-(4-Fluorobenzylamino)-10-hydroxyundecyl]-3,7-dimethylxanthine
1-[11-(4-Trifluoromethylbenzylamino)-10-hydroxyundecyl]-3,7-dimethylxanthine
1-[11-(3-Diethylaminopropylamino)-10-hydroxyundecyl]-3,7-dimethylxanthine
N,N'-bis [(10-yl-9-hydroxydecyl)-3,7-dimethylxanthine]-diaminododecane
1-(14-Bromo-13-hydroxytetradecyl)-3,7-dimethylxanthine
1-[11-(4-Aminobenzylamino)-10-hydroxyundecyl]-3,7-dimethylxanthine
1-[11-(3,4,5-Trimethoxybenzylamino)-10-hydroxyundecyl]-3,7-dimethylxanthine
1-[11-(3-Butoxypropylamino)10-hydroxyundecyl)-3,7-dimethylxanthine
1-(14-Octylamino-13-hydroxytetradecyl)-3,7-dimethylxanthine
1-(11-Propylamino-10-hydroxyundecyl)-3,7-dimethylxanthine
1-(11-Undecylamino-10-hydroxyundecyl-3,7-dimethylxanthine
1-(11-Phenylamino-10-hydroxyundecyl)-3,7-dimethylxanthine
N,N-bis[11-yl-10-hydroxyundecyl)-3,7-dimethylxanthine] undecylamine
1-(11-Octadecylamino-10-hydroxyundecyl)-3,7-dimethylxanthine
1-[9-(N-Methyloctylamino-8-hydroxynonyl)]-3,7-dimethylxanthine
1-(4-Tetradecylamino-3-hydroxybutyl)-3,7-dimethylxanthine
1-[9-(2-hydroxydecyl-1-amino)nonyl]-3,7-dimethylxanthine
1-(6-Octadecylamino-5-hydroxyhexyl)-3,7-dimethylxanthine
1-[11-(N-Octylacetamido)10-hydroxyundecyl]-3,7-dimethylxanthine
2-(11-Octylamino-10-hydroxyundecyl)-N-methylbenzamide
1-(11-(N-Methyl-N-octylamino)-10-hydroxyundecyl)-3,7-dimethylxanthine
N-(11-Octylamino-10-hydroxyundecyl)-piperidine
2-(11-Octylamino-10-hydroxyandecyl)-1,3-dihydroxybenzene
1-[11-Amino-10-hydroxyundecyl)-3,7-dimethylxanthine
1-(11-Hexadecylamino-10-hydroxyundecyl)-3,7-dimethylxanthine
1-(11-Tridecylamino-10-hydroxylundecyl)-3,7-dimethylxanthine
1-[11-Dihexylamino-10-hydroxyundecyl)-3,7-dimethylxanthine
1-(11-Pentadecylamino-10-hydroxyundecyl)-3,7-dimethylxanthine
1-[11-(N,N-Diethanolamino)undecyl]-3,7-dimethylxanthine
1-[11-(2-Piperidinoethylamino)-10-hydroxyundecyl]-3,7-dimethylxanthine
1-[11-(4-Methyl-1-yl-piperazino)-10-hydroxyundecyl]-3,7-dimethyxanthine
1-[11-Hydroxy-10-aminoundecyl]-3,7-dimethylxanthine
1-[11-(4-Chlorobenzyl)-10-hydroxyundecyl]-3,7-dimethylxanthine
1-[11-(2,4,6-Trimethoxybenzylamino)-10-hydroxyundecyl]-3,7-dimethylxanthine
1-(11-tert-Butylamino-10-hydroxyundecyl)-3,7-dimethylxanthine
6-(11-dodecylamino-10-hydroxyundecoxy)-2-hydroxy-3,7-methylpurine
N,N-bis-[(11-yl-10-hydroxyundecyl)-3,7-dimethylxanthine]-dodecylamine
1-[11-(3,4,5-Trimethoxyphenylamino)-10-hydroxyundecyl]-3,7-dimethylxanthine
1-[11-(N-Methyl-N-dodecylamino)-10-hydroxyundecyl]-3,7-dimethylxanthine
1-[11-(N-Dodecylacetamido)-10-hydroxyundecyl]-3,7-dimethylxanthine
1-[11-(N-Tetradecylacetamido)-10-hydroxyundecyl]-3,7-dimethylxanthine
1-[11-(3,4,5-Trimethoxybenzylacetamido)-10-hydroxyundecyl]-3,7-dimethylxanthine
1-[11-(N-Dodecylacetamido)-10-acetoxyundecyl]-3,7-dimethylxanthine
1-[11-(N-Methyl-N-dodecylamino)-10-acetoxyundecyl]-3,7-dimethylxanthine
1-[11-(Morpholine-4-yl)-10-hydroxyundecyl]-3,7-dimethylxanthine
1-[11-(Dodecylbenzamido)-10-hydroxyundecyl]-3,7-dimethylxanthine
1-[11-(3,5-Dimethoxybenzylamino)-10-hydroxyundecyl]-3,7-dimethylxanthine
1-[7-(3-Octyl-2-oxo-5-oxazolidinyl)heptyl]-3,7-dimethylxanthine
1-[9-(N-Dodecyl-2-oxazolidin-5-yl)nonyl]-3,7-dimethylxanthine Synthesis of the Long Chain Amino Alcohol Compounds An exemplary method for preparing the long chain amino alcohol compounds provides a long chain amino alcohol compound containing a desired terminal group (intended as a "terminal moiety" in compounds of the invention) undergoes a reaction to produce an anion of the terminal moiety-containing compound. Subsequently, the resulting anion is reacted with a substituted olefin to displace a targeted functional group on the olefin, resulting in an intermediate product. A predetermined amount of a terminal moiety-containing compound is reacted with a suitable base, a solvent and a substituted olefin, the substituted olefin having at least one other functional group which may be substituted in a displacement reaction by the desired terminal moiety-containing compound.

Preferred bases include, but are not limited to, sodium hydride, sodium amide, sodium alkoxide, lithium hydride, potassium hydride, lithium amide, sodium amide and potassium amide. Preferred solvents may be dimethylsulfoxide, dimethylformamide, or an alcohol. Exemplary preferred alcohols include, but are not limited to, methanol, ethanol or isopropanol. Any substituted olefin comprising a chain structure of the long chain amino alcohol compounds may be used in the reaction. Preferred olefins may be ω-substituted olefins. Preferred substituted olefins include, but are not limited to halo-substituted olefins.

The intermediate product, having a composite structure of the terminal moiety-containing compound and substituted olefin, may subsequently be converted to a corresponding epoxide. In the method, the intermediate product may be reacted with an organic peracid to obtain a desired epoxide. Preferred, exemplary organic peracids include 3-chloroperoxybenzoic acid, peracetic acid and trifluoroperacetic acid.

Alternatively, the intermediate product may be converted first to a corresponding diol by reacting the intermediate product with a suitable oxidizing agent. Preferred oxidizing agents include, but are not limited to, osmium tetroxide. Preferred oxidizing agents, such as osmium tetroxide may require a catalytic amount of the oxidizing agent in the presence of a regenerating agent. Exemplary, regenerating agents may be 4-methylmorpholine-N-oxide and trimethylamine-N-oxide. In a subsequent halogenation reaction, the resulting diol is converted to a haloester using a halogenating agent in the presence of an organic acid. Exemplary halogenating agents include hydrogen bromide and hydrogen chloride. Preferred organic acids may be acetic acid and propionic acid. The resulting haloester is subsequently reacted with a basic ester-hydrolyzing reagent to obtain a desired epoxide product. Preferred ester-hydrolyzing agents include, but are not limited to metal alkoxides and metal hydroxides. Especially preferred metal alkoxides are sodium methoxide, ethoxide, isopropoxide and pentoxide. A preferred metal hydroxide is sodium hydroxide.

A final step in the method is preparation of the desired long chain amino alcohol compound from a terminal moiety-containing epoxide, synthesized in the foregoing procedure. The final step may be accomplished by either of two preferred methods. In a first method, the terminal moiety-containing epoxide is heated in the presence of a substituted or unsubstituted amine having functional groups which are present in the final long chain amino alcohol compound. Preferred amine functional groups are disclosed above.

A second method comprises reacting the unsubstituted or substituted amine with the terminal moiety-containing epoxide and a reaction activator in a solvent. Exemplary reaction activators include lithium perchlorate. Preferred solvents include solvents for reactions previously discussed herein.

Formulation and Dosage

It will be recognized by one of skill in the art that the form and character of the pharmaceutically acceptable carrier or diluent is dictated by the amount of active ingredient with which it is to be combined, the route of administration and other well-known variables. A MDR reversing formulation is administered to a patient in an amount sufficient to reverse the MDR phenotype in a patient in need of such treatment. A MDR reversing formulation can be administered to such human in a conventional dosage form prepared by combining the long chain amino alcohol compound with a conventional pharmaceutically acceptable carrier or diluent according to known pharmaceutical formulation techniques. The route of administration of the formulation is not critical but is usually oral or parenteral, preferably parenteral to the site of tumor. Preferably, the long chain amino alcohol compound is administered parenterally. The term parenteral, as used herein, includes intravenous, intramuscular, subcutaneous, intranasal, intrarectal, transdermal, opthalmic, intravaginal or intraperitoneal administration.

The subcutaneous and intramuscular forms of parenteral administration are generally preferred. The daily parenteral dosage regimen will preferably be from about 0.01 mg/kg to about 25 mg/kg of total body weight, most preferably from about 0.1 mg/kg to about 4 mg/kg. Preferably, each parenteral dosage unit will contain the active ingredient in an amount of from about 0.1 mg to about 400 mg. The long chain amino alcohol compounds are generally active when given orally and can be formulated as liquids, for example, syrups, suspensions or emulsions, tablets, capsules and lozenges. A liquid formulation will generally consist of a suspension or solution of the compound or pharmaceutically acceptable salt in a suitable liquid carrier(s), for example, ethanol, glycerine, non-aqueous solvent, for example polyethylene glycol, oils, or water with a suspending agent, preservative, flavoring or coloring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule. Alternatively, a dispersion or suspension can be prepared using any suitable pharmaceutical carrier(s), for example, aqueous gums, celluloses, silicates or oils and the dispersion or suspension then filled into a soft gelatin capsule. The daily oral dosage regimen will preferably be from about 0.01 mg/kg to about 40 mg/kg of total body weight. Preferably, each oral dosage unit will contain the active ingredient in an amount of from about 0.1 mg to about 1000 mg.

It will be recognized by one of skill in the art that the optimal quantity and spacing of individual dosages of a compound or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment (i.e., the number of doses of a compound or a pharmaceutically acceptable salt or hydrate or solvate thereof given per day and duration of therapy) can be ascertained by those skilled in the art using conventional course of treatment determination tests.

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1

This example illustrates cytotoxic sensitization of P388/MDR cells by preincubation with a subcytotoxic concentration of CT-2584(1.3 µM). The murine monocytic leukemia cell line P388/MDR is highly amplified in pgp-1 and is approximately 100–500-fold more resistant to doxorubicn than the parental P388 cell line. P388/MDR is also cross resistant to a variety of DNA intercalating agents in addition to doxorubicin, including actinomycin D (RI=8), azetomycin II (RI=21), mithramycin (RI=64), ellipticine (RI =30), chartreusin (RI=80), nitidine (R=8.6), coralyne (RI=100), and synthetic agents hycanthone (RI=3), and AMSA (RI=7). In addition P388/MDR cells are cross resistant to a number of mitotic spindle inhibitors such as vincristine (RI=9.5), vinblastine (RI=8.3), vindensine (RI=8.9), VM-26 (RI>12.5), etoposide (RI=17), maytansine (RI=7.6), oncodazole (RI=3.0) as well as cross resistance to a number of inhibitors of protein biosynthesis (RI range from 2–58) (Johnson et al., *Cancer Treatment Reports* 62: 1535–1547, 1978).

Figure 2:
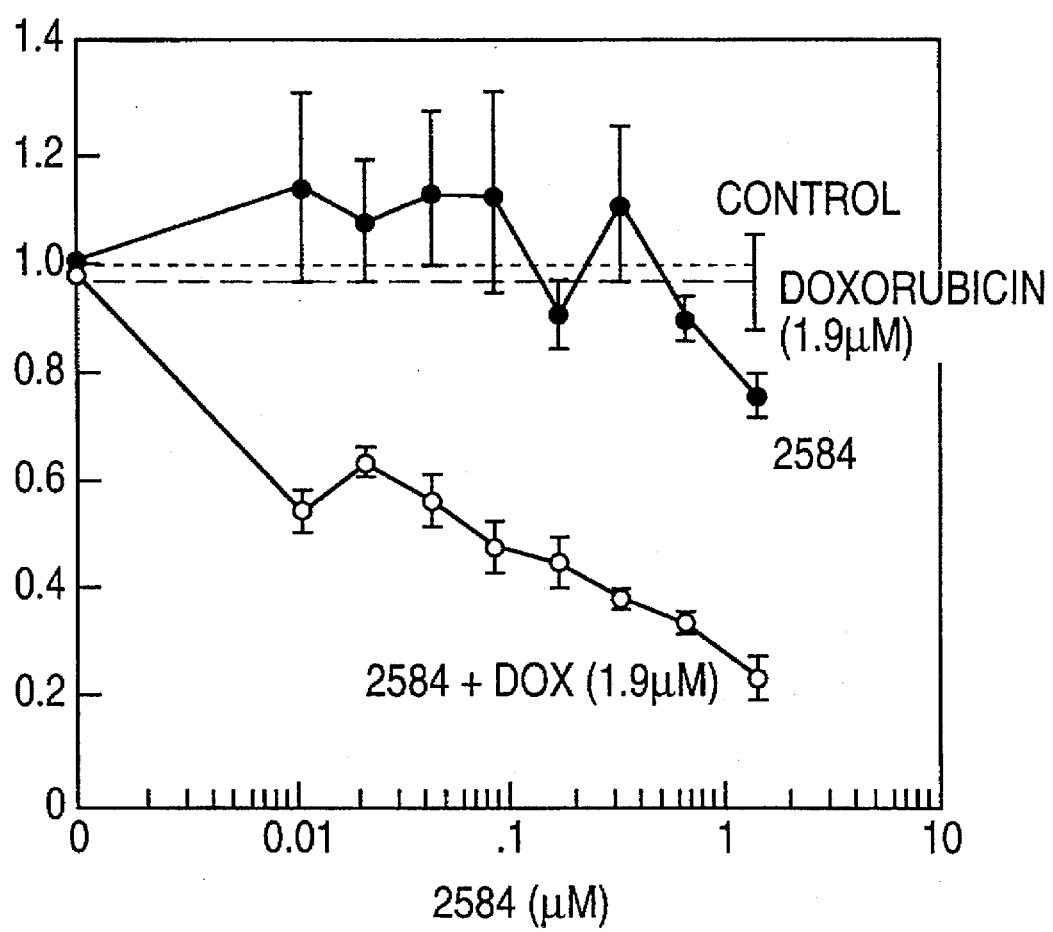
FIG. 2 shows a dose response for CT-2584 sensitization. P388/MDR cells were incubated with a subcytotoxic dose of doxorubicin (1.9 μM) and pretreated with various concentrations of CT-2584. Sensitization to doxorubicin by CT-2584 was observed at a 10 nM concentration of CT-2584.

Cells were treated with CT-2584 at 0, 0.1, 0.5, 1 and 2 µM for 1 hr prior to addition of Doxorubicin at 1 of 0.5 µM and cells were incubated at 37 ° C. for 1 hr. FIG. 1 shows that preincbation with CT-2584 reversed inherent doxorubicn resistance of P388/MDR. The parent cell line, P388, was not sensitized significantly by preincubation with CT-2584. FIG. 2 shows a dose response for CT-2584 sensitization. P388/MDR cells were incubated with a subcytotoxic dose of doxorubicn (1.9 µM) and pretreated with various concentrations of CT-2584. Sensitization to doxorubicin by CT-2584 was evident even at a 10 nM concentration of CT-2584.

Figure 3:
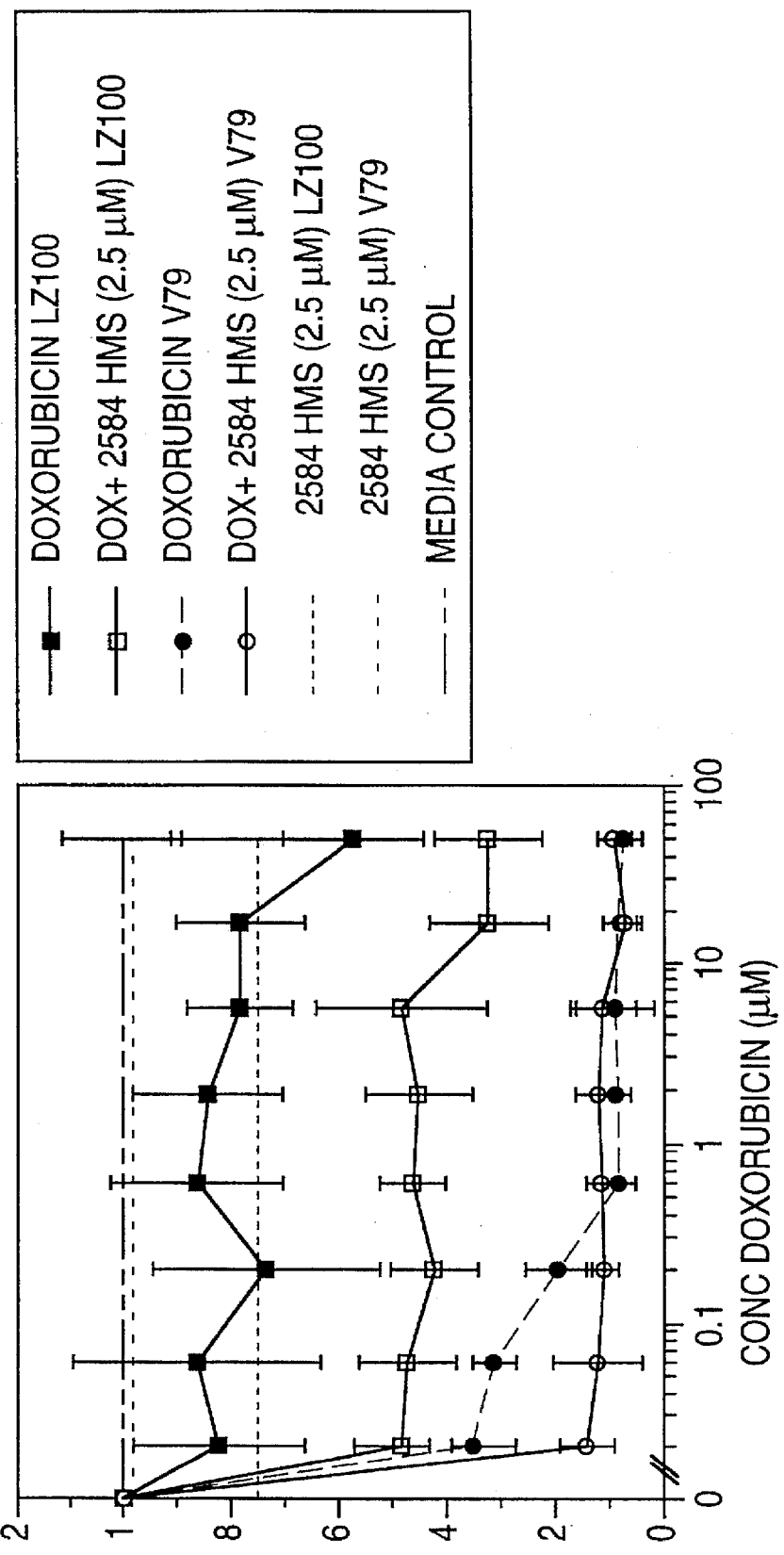
FIG. 3 shows sensitization of LZ100 cells by CT-2584 to doxorubicin. The Chinese hamster cell line LZ100/DX has a 9000-fold resistance index (RI) to doxorubicin. These cells express large amounts of pgp-1. Up to 20% of the plasma membrane proteins derived from these cells consists of pgp-1. LZ100 cells were sensitized to the cytotoxic actions of doxorubicin by preincubation with 2.5 μM of CT-2584.

FIG. 3 shows sensitization of LZ100 cells by CT-2584 to doxorubicin. The Chinese hamster cell line LZ100/DX derived from the V79 parent (Sognier et al., *Biochem. Pharmacol.* 44:1859–1868, 1992) has a 9000-fold resistance index (RI) to doxorubicin. These cells express large amounts of pgp-1. Up to 20% of the plasma membrane proteins derived from these cells consists of pgp-1 (Sognier et al., *Biochem. Pharmacol.* 44:1859–1868, 1992). However, additional mechanisms of drug resistance are operational in the LZ100/DX cells including altered drug sequestration (Sognier et al., *Biochem. Pharmacol.* 48:391–401, 1994), lower topoisomerase activity and inactivation of doxorubicin by structural conversion to a noncytotoxic metabolite (Zhang et al., *Biochem. Pharmacol.* 44:1869–1877, 1992). LZ100/DX cells are cross resistant to daurnorubicin, mitoxantrone, etoposide, paclitaxel, colchicine, vincristine, actinomycin D and colcemid. As shown in FIG. 3, LZ100 cells were sensitized markedly to the cytotoxic actions of doxorubicn by preincubation with 2.5 µM CT-2584.

Figure 4:
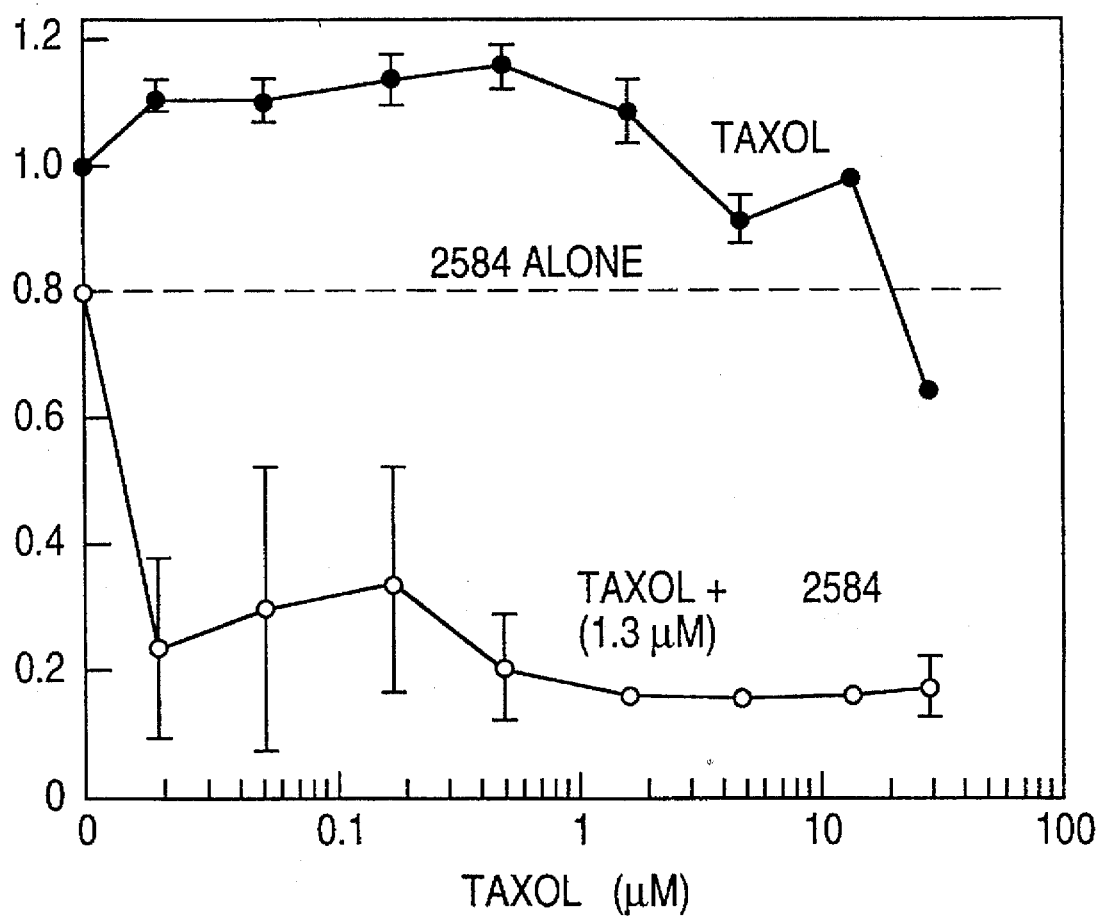

As shown in FIG. 4, cytotoxic enhancement by CT-2584 can take place with other agents which are transported by the P-glycoprotein membrane pump. LZ100 cells are markedly sensitized to paclitaxel by preincubation with CT-2584 (1.3 µM). LZ100 cells are sensitized to colchicine (FIG. 5) as well as actinomycin D (FIG. 6), with only small enhancement with the parental, non pgp-1 amplified, V-79 cells in either case (as would be expected by specific inhibition of pgp-1 ).

Figure 9:
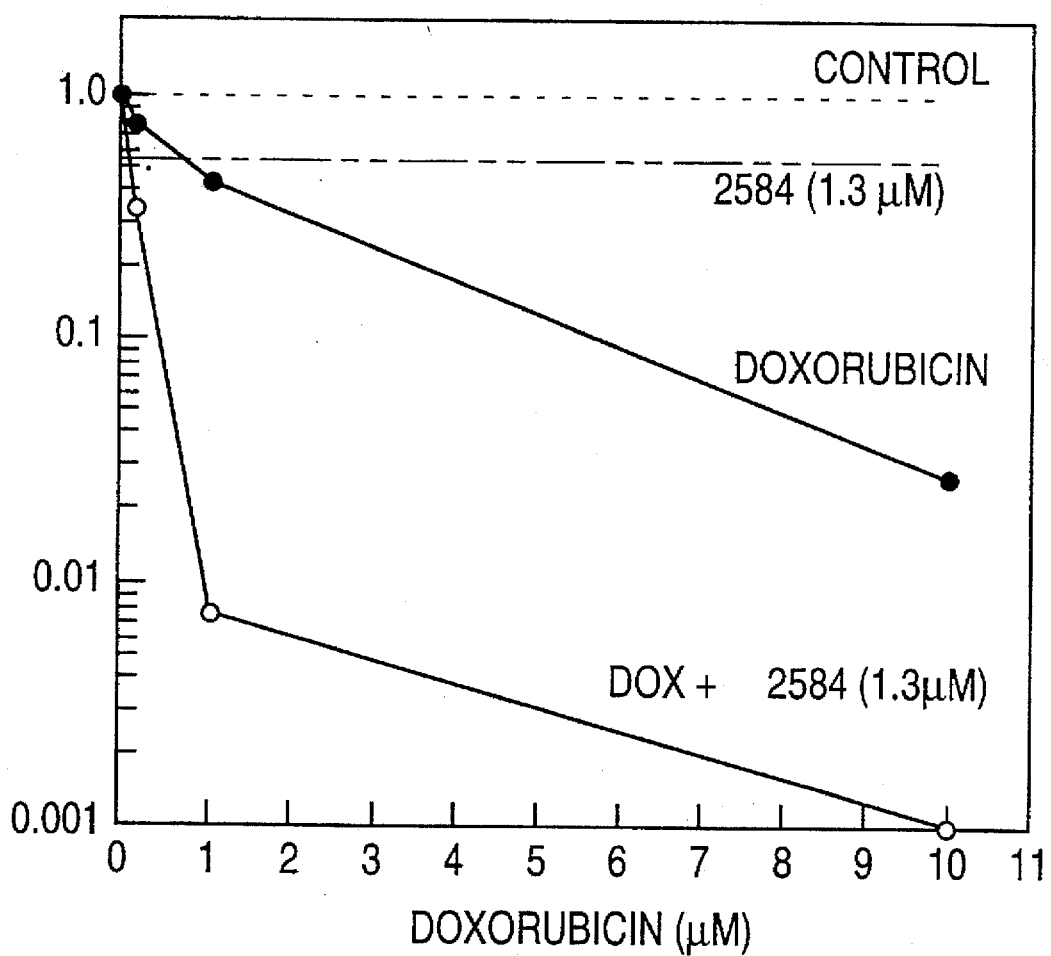
FIG. 9 shows sensitization of MCF-7/ADR to doxorubicin by a colony forming assay. Pre-incubation with a sub-cytotoxic dose of CT-2584 enhanced tumor survival to doxorubicin (as measured by colony formation) by approximately 100-fold.

The human breast carcinoma cell line MCF-7/ADR derived from the MCF-7 parent grown in the presence of doxorubicin (Batist et al., *J. Biol. Chem.* 261:15544–15549, 1986). The cells display the typical MDR phenotype, expressing elevate mdr-1 and gp170 (Moscow et al., *Cancer Res.* 49:1422–1428, 1989) and are cross resistant to actinomycin D (RI=357), vinblastine (RI=274), vincristine (RI>170) and etoposide (RI=175) (Johnson et al., *Cancer Treatment Reports* 62:1535–1547, 1978). In addition, the MCF-7/ADR cells have a 45-fold increase in a GSH transferase activity and expression of a novel glutathione S-transferase (GST) isoenzyme related to a marker isoenzyme found in hyperplastic liver nodules following carcinogen treatment in rats (Johnson et al., *Cancer Treatment Reports* 62: 1535–1547, 1978; and Moscow et al., *Cancer Res.* 49:1422–1428, 1989). Thus resistance in the MCF-7/ADR is thought to involve both increased drug efflux swell as greater detoxification of intracellular drugs. As shown in FIG. 7, MCF-7 cells are also sensitized to doxorubicin by preincubation with CT-2584 (1.31 µM) while the sensitive and non-amplified or over expressing parental line, MCF-7, is not. Further more, as shown in FIG. 8, MCF-7/ADR cells are sensitized to paclitaxel by preincubation with CT-2584 (1.3 µM). Sensitization of MCF-7/ADR to doxorubicn was confirmed by a colony forming assay (FIG. 9) which shows that pre-incubation with a subcytotoxic dose of CT-2584 can enhance tumor survival to doxorubicn (as measured by colony formation) by approximately 100-fold.

P388/DX Johnson were placed at $5 \times 10^{-5}$/mL in RPMI 1640 Media supplemented with, 10% fetal bovine serum, 1% penicillin-streptomycin and 1% L-glutamine. Following preparation, cells were treated with CT-2584 at 0, 0.5 and 1 µM for 1 hr prior to addition of Doxorubicin at 0, 0.5, 1, 10 and 50 µM and cells were incubated at 37° C. for 1 hr. Following treatment cells were placed on ice immediately, washed twice and resuspended in complete medium. Following washing the cells were either analyzed immediately or placed back at 37° C. for an additional 30 minutes. All the resulting samples were run on ELITE flow cytometer (Coulter, Electronics Inc.) to detect doxorubicin fluorescence with excitation of 488 nm and emission at 560 nm (+/−25 nm) wavelength. Relative fluorescence was determined by dividing the fluorescence value of the treated samples by the fluorescence value of untreated samples.

Figure 10B:
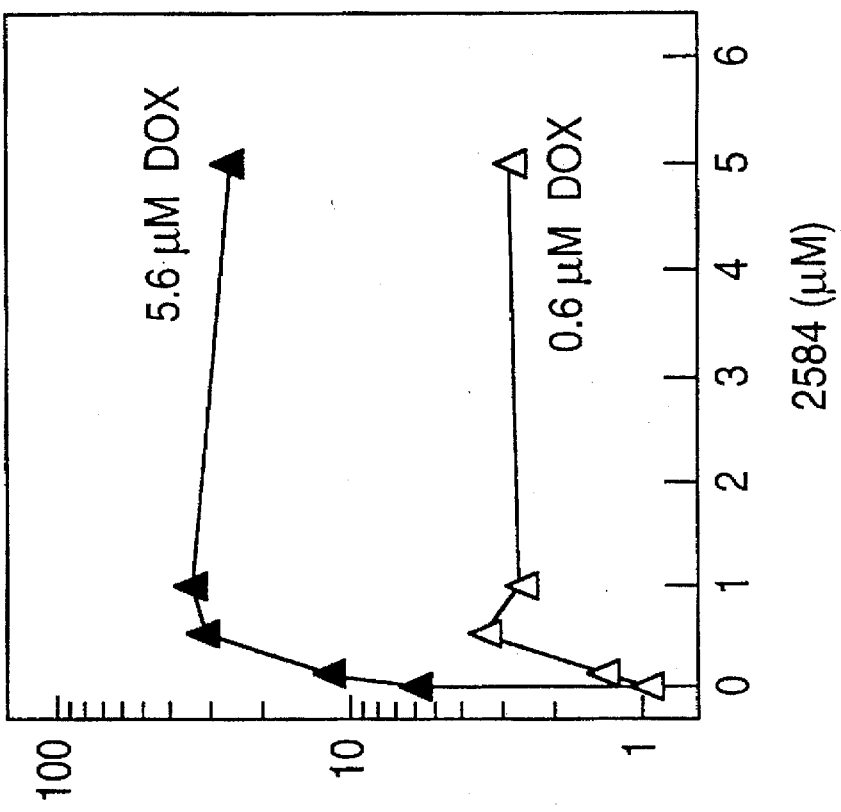
FIG. 10 shows that CT-2584 acted by enhancing doxorubicin (Dox) uptake in P388/MDR cells by inhibition of pgp-1. Cells were incubated with doxorubicin. Endogenous fluorescence was measured by flow cytometry. CT-2584 enhanced doxorubicin uptake at all concentrations of doxorubicin or CT-2584 tested. AT 1.3 μM CT-2584, the enhancement in doxorubicin retention was approximately 10-fold.
Figure 10A:
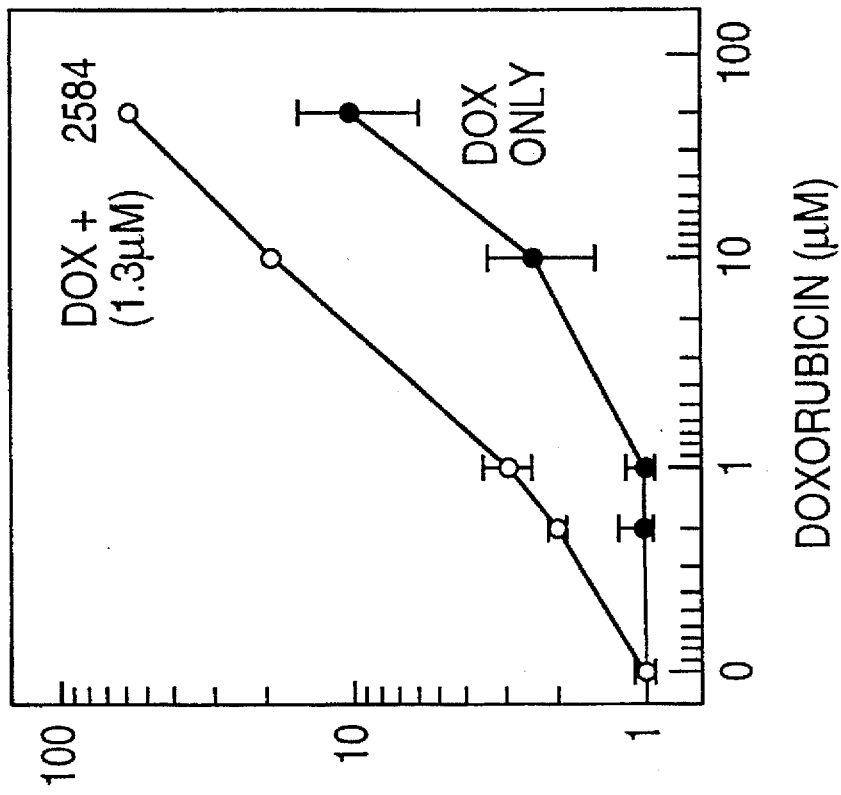

Finally FIG. 10 shows that CT-2584 acts by enhancing doxorubicn uptake in P388/MDR cells by inhibition of pgp-1. Cells were incubated with doxorubicin and endogenous fluorescence measured by flow cytometry. CT-2584 is shown to enhance doxorubicin uptake at all concentrations of doxorubicin or CT-2584 tested. AT 1.3 µM CT-2584, the enhancement in doxorubicin retention was approximately 10-fold.

We claim:

1. A method for reversing multiple drug resistance (MDR) phenotype in tumors insensitive to hydrophobic chemotherapeutic drugs due to over expression of mdr-1, comprising administering an effective amount of a long chain amino alcohol compound, wherein the long chain amino alcohol compound includes resolved enantiomers, resolved diastereomers, hydrates, salts, solvates or mixtures thereof from formula I or from formula II: formula I

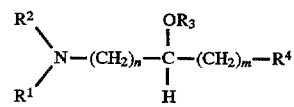

wherein n is an integer from one to four and m is an integer from four to twenty, $R_1$ and $R_2$ are independently hydrogen, a straight or branched chain alkyl, alkenyl or alkynyl of up to twenty carbon atoms in length or —$(CH_2)_wR_5$, wherein if $R_1$ or $R_2$ is —$(CH_2)_2R_5$, w is an integer from one to twenty and $R_5$ is an hydroxyl, halo, or $C_{1-8}$ alkoxyl group, $R_1$ and $R_2$ jointly form a saturated or unsaturated heterocyclic having from four to eight carbon atoms, $R_3$ is hydrogen or $C_{1-3}$, wherein a total sum of carbon atoms comprising $R_1$ and $R_2$, $(CH_2)_n$ and $(CH_2)_m$ does not exceed forty, $R_4$ is a heterocyclic moiety having from 4–7 atoms, including a nitrogen atom in one ring or two fused rings; or formula II

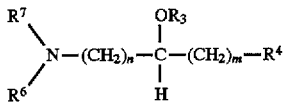

wherein n, m, $R_3$, and $R_4$ are defined as provided in formula I, $R_6$ and $R_7$ are hydrogen, a straight or branched chain alkane, alkene or alkyne of up to twenty carbon atoms in length, or —$(CH_2)_xR_8$, at least one of $R_6$ or $R_7$ is —$(CH_2)_2R_8$, x is an integer from zero to fourteen and $R_8$ is a moiety having a general structure as provided in formula III

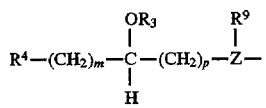

wherein m, $R_3$, and $R_4$ are defined as provided in formula I, Z is N or Ch, p is an integer from zero to four, and $R_9$ is H or a straight or branched chain alkane, alkene or alkyne of up to twenty carbon atoms in length.

2. The method for reversing MDR phenotype of claim 1 wherein the long chain amino alcohol compound is selected from the group consisting of N-(9-Octylamino-8-hydroxynonyl)-phthalimide, N-(11-Octylamino-10-hydroxyundecyl)-homophthalimide, 1-(5-hydroxy-6-(N-benzyl)aminohexyl)-3-methylbenzoyleneurea, 3-(11,10-Oxidoundecyl)-quinazoline-4(3H)-one, $N^2$-(5-hydroxy-6-($N^3$-propyl)-aminohexyl)-($N^1$-propyl)-glutaric acid, 2-(11-Octylamino-10-hydroxyundecylcarboxamido)-octylcarboxamidobenzyl, 1-Octylamino-2,11-undecadiol, 1-(9-Octylamino-8-hydroxynonyl)-3-methylxanthine, 1-(9-Tetradecylamino-8-hydroxynonyl)-3-methylxanthine, 1-(11-Octylamino-10-hydroxyundecyl)-3-methylxanthine, 7-(11-Octylamino-10-hydroxyundecyl)-1,3-dimethylxanthine, 1-(11,10-Octylamino-10-hydroxyundecyl)-1-methyl-2,4-dioxotetrahydropteridine, 1-(5-hydroxy-6-(N-benzyl)aminohexyl)-3,7-dimethylxanthine, 1-(5-hydroxy-6-(N-propyl)aminohexyl)-3,7-dimethylxanthine, N-(11-Ocytlamino-10-hydroxyundecyl)-glutarimide, N-(11-Octylamino-10-hydroxyundecyl)-2-piperidone, N-(11-Octylamino-10-hydroxyundecyl)-succinimide, 2-(11-Octylamino-10-hydroxyundecyl)-1,3-dimethoxybenzene, 3-(5-hydroxy-6-(N-propyl)aminohexyl)-1-methyluracil, 3-(9-Octylamino-8-hydroxynonyl)-1-methyluracil, 3-(11-Octylamino-10-hydroxyundecyl)-1-methyluracil, 3-(11-Octylamino-10-hydroxyundecyl)-1-methyldihydrouracil, 3-(9-Octylamino-8-hydroxynonyl)-1-methylthymine, 3-(5-hydroxy-6-(N-undecyl)aminohexyl)-1-methylthymine, 3-(11-Octylamino-10-hydroxyundecyl)-1-methylthymine, 3-(6-Propylamino-5-hydroxyhexyl)-1-methylthymine, 1-(8-hydroxy-9-(N-benzyl)aminononyl)-3,7-dimethylxanthine, 1-(5-hydroxy-6-(N-octyl)aminohexyl)-3,7-dimethylxanthine, 1-(5-hydroxy-6-(N-(4-phenyl)butyl)aminohexyl)-3,7-dimethylxanthine, 1-(6-Undecylamino-5-hydroxyhexyl)-3,7-dimethylxanthine, 1-(5-hydroxy-6-(N-cyclohexylmethyl)aminohexyl)-3,7-dimethylxanthine, 1-(5-hydroxy-6-(N-(6-hydroxy)hexyl)aminohexyl)-3,7-dimethylxanthine, 1-(5-hydroxy-6-(N,N-dihexyl)aminohexyl)-3,7-dimethylxanthine, 1-(5-hydroxy-6-(N-(4-methoxy)benzyl)aminohexyl)-3,7-dimethylxanthine, 1-(8-hydroxy-9-(N-octyl)aminononyl)-3,7-dimethylxanthine, 1-(5-hydroxy-6-(N-tetradecyl)aminohexyl)-3,7-dimethylxanthine, 1-[6-(Cyclopropylmethylamino)-5-hydroxyhexyl)]-3,7-dimethylxanthine, 1-(6-Decylamino-5-hydroxyhexyl)-3,7-dimethylxanthine, 1-(6-Dodecylamino-5-hydroxyhexyl)-3,7-dimethylxanthine, 1-(11-Benzylamino-10-hydroxytndecyl-3,7-dimethylxanthine, 1-(9-Decylamino-8-hydroxynonyl)-3,7-di, 1-(9-Tetradecylamino-8-hydroxynonyl)-3,7-dimethylxanthine, 1-(11-Hexylamino-10-hydroxyundecyl)-3,7-dimethylxanthine, 1-(11-Octylamino-10-hydroxyundecyl-3,7-dimethylxanthine, 1-(6-Allylamino- 5-hydroxyhexyl)-3,7-dimethylxanthine, 1-(11-Allylamino-10-hydroxyundecyl)-3,7-dimethylxanthine, 1-(6-N-Methyloctadecylamino-5-hydroxyhexyl)-3,7-dimethylxanthine, 1-(11-Decylamino-10-hydroxyundecyl)-3,7-dimethylxanthine, 1-(11-Dodecylamino-10-hydroxyundecyl)-3,7-dmethylxanthine, 1-(11-Tetradecylamino-10-hydroxyundecyl)-3,7-dimethylxanthine, 1-[11-(4-Fluorobenzylamino)-10-hydroxyundecyl]-3,7-dimethylxanthine, 1-[11-(4-Trifluoromethylbenzylamino)-10-hydroxyundecyl]-3,7-dimethylxanthine, 1-[11-(3-Diethylaminopropylamino)-10-hydroxyundecyl]-3,7-dimethylxanthine, N,N'-bis[(10-yl-9-hydroxydecyl)-3,7-dimethylxanthine]-diaminododecane, 1-(14-Bromo-13-hydroxytetradecyl)-3,7-dimethylxanthine, 1-[11-(4-Aminobenzylamino)-10-hydroxyundecyl]-3,7-dimethylxanthine, 1-[11-(3,4,5-Trimethoxybenzylamino)-10-hydroxytndecyl]-3,7-dimethylxanthine, 1-[11-(3-Butoxypropylamino)10-hydroxyundecyl)-3,7-dimethylxanthine, 1-(14-Octylamino-13-hydroxytetradecyl)-3,7-dimethylxanthine, 1-(11-Propylamino-10-hydroxyundecyl)-3,7-dimethylxanthine, 1-(11-Undecylamino-10-hydroxyundecyl-3,7-dimethylxanthine, 1-(11-Phenylamino-10-hydroxyundecyl)-3,7-dimethylxanthine, N,N-bis [11-yl-10-hydroxyundecyl)-3,7-dimethylxanthine]undecylamine, 1-(11-Octadecylamino-10-hydroxytndecyl)-3,7-dimethylxanthine, 1-[9-(N-Methyloctylamino-8-hydroxynonyl)]-3,7-dimethylxanthine, 1-(4-Tetradecylamino-3-hydroxybutyl)-3,7-dimethylxanthine, 1-[9-(2-hydroxydecyl-1-amino)nonyl]-3,7-dimethylxanthine, 1-(6-Octadecylamino-5-hydroxyhexyl)-3,7-dimethylxanthine, 1-[11-(N-Octylacetamido)10-hydroxyundecyl]-3,7-dimethylxanthine, 2-(11-Octylamino-10-hydroxyundecyl)-N-methylbenzamide, 1-(11-(N-Methyl-N-octylamino)-10-hydroxyundecyl)-3,7-dimethylxanthine, N-(11-Octylamino-10-hydroxyundecyl)-piperidine, 2-(11-Octylamino-10-hydroxyundecyl)-1,3-dihydroxybenzene, 1-[11-Amino-10-hydroxyundecyl)-3,7-dimethylxanthine, 1-(11-Hexadecylamino-10-hydroxyandecyl)-3,7-dimethylxanthine, 1-(11-Tridecylamino-10-hydroxylundecyl)-3,7-dimethylxanthine, 1-[11-Dihexylamino-10-hydroxyundecyl)-3,7-dimethylxanthine, 1-(11-Pentadecylamino-10-hydroxytndecyl)-3,7-dimethylxanthine, 1-[11-(N,N-Diethanolamino)undecyl]-3,7-dimethylxanthine, 1-[11-(2-Piperidinoethylamino)-10-hydroxyundecyl]-3,7-dimethylxanthine, 1-[11-(4-Methyl-1-yl-piperazino)-10- hydroxyundecyl]-3,7-dimethyxanthine, 1-[11-Hydroxy-10-aminoundecyl]-3,7-dimethylxanthine, 1-[11-(4-Chlorobenzyl)-10-hydroxyundecyl]-3,7-dimethylxanthine, 1-[11-(2,4,6-Trimethoxybenzylamino)-10-hydroxyundecyl]-3,7-dimethylxanthine, 1-(11-tert-Butylamino-10-hydroxyundecyl)-3,7-dimethylxanthine, 6-(11-dodecylamino-10-hydroxyundecoxy)-2-hydroxy-3,7-methylpurine, N,N-bis-[(11-yl-10-hydroxyundecyl)-3,7-dimethylxanthine]-dodecylamine, 1-[11-(3,4,5-Trimethoxyphenylamino)-10-hydroxytmdecyl]-3,7-dimethylxanthine, 1-[1 I-(N-Methyl-N-dodecylamino)-10-hydroxyundecyl]-3,7-dimethylxanthine, 1-[11-(N-Dodecylacetamido)-10-hydroxyundecyl]-3,7-dimethylxanthine, 1-[11-(N-Tetradecylacetamido)-10-hydroxyundecyl]-3,7-dimethylxanthine, 1-[11-(3,4,5-Trimethoxybenzylacetamido)-10-hydroxyundecyl]-3,7-dimethylxanthine, 1-[11-(N-Dodecylacetamido)-10-acetoxyundecyl]-3,7-dimethylxanthine, 1-[11-(N-Methyl-N-dodecylamino)-10-acetoxyundecyl]-3,7-dimethylxanthine, 1-[11-(Morpholine-4-yl)-10-hydroxytmdecyl]-3,7-dimethylxanthine, 1-[11-(Dodecyl benzamido)-10-hydroxyundecyl]-3,7-dimethylxanthine, 1-[11-(3,5-Dimethoxybenzylamino)-10-hydroxyundecyl]-3,7-dimethylxanthine, 1-[7-(3-Octyl-2-oxo-5-oxazolidinyl) heptyl]-3,7-dimethylxanthine, and 1-[9-(N-Dodecyl-2-oxazolidin-5-yl)nonyl]-3,7-dimethylxanthine.

3. The method for reversing MDR phenotype of claim 2 wherein the long chain amino alcohol compound is 1-(11-Dodecylamino-10-hydroxyundecyl)-3,7-dmethylxanthine.

4. A method for inducing cytotoxic sensitization to cancer chemotherapeutic agents, comprising administering an effective amount of a long chain amino alcohol compound, wherein the long chain amino alcohol compound includes resolved enantiomers, resolved diastereomers, hydrates, salts, solvates or mixtures thereof from formula I or from formula II:

formula I

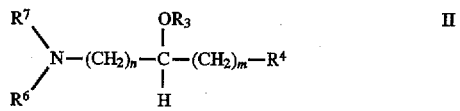

wherein n is an integer from one to four and m is an integer from four to twenty, $R_1$ and $R_2$ are independently hydrogen, a straight or branched chain alkyl, alkenyl or alkynyl of up to twenty carbon atoms in length or —$(CH_2)_w R_5$, wherein if $R_1$ or $R_2$ is —$(CH_2)_w R_5$, w is an integer from one to twenty and $R_5$ is an hydroxyl, halo, or $C_{1-8}$ alkoxyl group, $R_1$, and $R_2$ jointly form a saturated or unsaturated heterocycle having from four to eight carbon atoms, $R_3$ is hydrogen or $C_{1-3}$, wherein a total sum of carbon atoms comprising $R_1$ and $R_2$, $(CH_2)_n$ and $(CH_2)_m$ does not exceed forty, $R_4$ is a heterocyclic moiety having from 4–7 atoms, including a nitrogen atom in one ring or two fused rings; or formula II

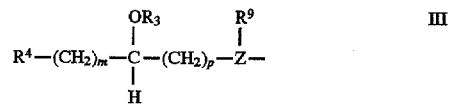

wherein n, m, $R_3$, and $R_4$ are defined as provided in formula I, $R_5$ and $R_7$ are hydrogen, a straight or branched chain alkane, or alkyne of up to twenty carbon atoms in length, or —$(CH_2)_x R_8$, at least one of $R_6$ or $R_7$ is —$(CH_2)_x R_8$, x is an integer from zero to fourteen and $R_8$ is a moiety having a general structure as provided in formula III

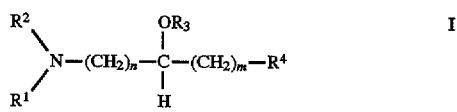

wherein m, $R_3$, and $R_4$ are defined as provided in formula I, Z is N or CH, p is an integer from zero to four, and $R_9$ is H or a straight or branched chain alkane, alkene or alkyne of up to twenty carbon atoms in length.

5. The method for preventing development of MDR during cancer chemotherapy of claim 4 wherein the long chain amino alcohol compound is selected from the group consisting of N-(9-Octylamino-8-hydroxynonyl)-phthalimide, N-(11-Octylamino-10-hydroxyundecyl)-homophthalimide, 1-(5-hydroxy-6-(N-benzyl)aminohexyl)-3-methylbenzoyleneurea, 3-(11,10-Oxidoundecyl)-quinazoline-4(3H)-one, $N^2$-(5-hydroxy-6-($N^3$-propyl)-aminohexyl)-($N^1$-propyl) glutaric acid, 2-(11-Octylamino-10-hydroxyundecylcarboxamido)-octylcarboxamidobenzyl, 1-Octylamino-2,11-undecadiol, 1-(9-Octylamino-8-hydroxynonyl)-3-methylxanthine, 1-(9-Tetradecylamino-8-hydroxynonyl)-3-methylxanthine, 1-(11-Octylamino-10-hydroxyundecyl)-3-methylxanthine, 7-(11-Octylamino-10-hydroxytmdecyl)-1,3-dimethylxanthine, 1-(11,10-Octylamino-10-hydroxyundecyl)-1-methyl-2,4-dioxotetrahydropteridine, 1-(5-hydroxy-6-(N-benzyl) aminohexyl)-3,7-dimethylxanthine, 1-(5-hydroxy-6-(N-propyl)aminohexyl)-3,7-dimethylxanthine, N-(11-Ocytlamino-10-hydroxyundecyl)-glutarimide, N-(11-Octylamino-10-hydroxyundecyl)-2-piperidone, N-(11-Octylamino-10-hydroxyundecyl)-succinimide, 2-(11-Octylamino-10-hydroxyundecyl)-1,3-dimethoxybenzene, 3-(5-hydroxy-6-(N-propyl)aminohexyl)-1-methyluracil, 3-(9-Octylamino-8-hydroxynonyl)-1-methyluracil, 3-(11-Octylamino-10-hydroxyundecyl)-1-methyluracil, 3-(11-Octylamino-10-hydroxyandecyl)-1-methyldihydrouracil, 3-(9-Octylamino-8-hydroxynonyl)-1-methylthymine, 3-(5-hydroxy-6-(N-undecyl)aminohexyl)-1-methylthymine,

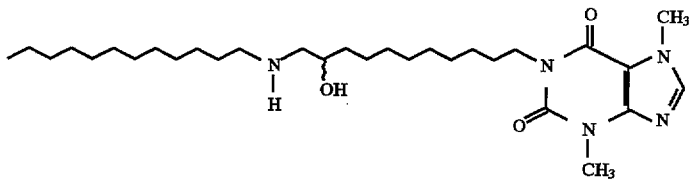

3-(11-Octylamino-10-hydroxyundecyl)-1-methylthymine, 3-(6-Propylamino-5-hydroxyhexyl)-1-methylthymine, 1-(8-hydroxy-9-(N-benzyl)aminononyl)-3,7-dimethylxanthine, 1-( 5-hydroxy-6-(N-octyl)aminohexyl)-3,7-dimethylxanthine, 1-(5-hydroxy-6-(N-(4-phenyl)butyl) aminohexyl)-3,7-dimethylxanthine, 1-(6-Undecylamino-5-hydroxyhexyl)-3,7-dimethylxanthine, 1-(5-hydroxy-6-(N-cyclohexylmethyl)aminohexyl)-3,7-dimethylxanthine, 1-(5-hydroxy-6-(N-(6-hydroxy)hexyl)aminohexyl)-3,7-dimethylxanthine, 1-(5-hydroxy-6-(N,N-dihexyl) aminohexyl)-3,7-dimethylxanthine, 1-(5-hydroxy-6-(N-(4-methoxy)benzyl)aminohexyl)-3,7-dimethylxanthine, 1-(8-hydroxy-9-(N-octyl)aminononyl)-3,7-dimethylxanthine, 1-(5-hydroxy-6-(N-tetradecyl)aminohexyl)-3,7-dimethylxanthine, 1-[6-(Cyclopropylmethylamino)-5-hydroxyhexyl)]-3,7-dimethylxanthine, 1-(6-Decylamino-5-hydroxyhexyl)-3,7-dimethylxanthine, 1-(6-Dodecylamino-5-hydroxyhexyl)-3,7-dimethylxanthine, 1-(11-Benzylamino-10-hydroxyundecyl-3,7-dimethylxanthine, 1-(9-Decylamino-8-hydroxynonyl)-3,7-di, 1-(9-Tetradecylamino-8-hydroxynonyl)-3,7-dimethylxanthine, 1-(11-Hexylamino-10-hydroxyundecyl)-3,7-dimethylxanthine, 1-(11-Octylamino-10-hydroxyundecyl-3,7-dimethylxanthine, 1-(6-Allylamino-5-hydroxyhexyl)-3,7-dimethylxanthine, 1-(11-Allylamino-10-hydroxyundecyl)-3,7-dimethylxanthine, 1-(6-N-Methyloctadecylamino-5-hydroxyhexyl)-3,7-dimethylxanthine, 1-(11-Decylamino-10-hydroxyundecyl)-3,7-dimethylxanthine, 1-(11-Dodecylamino-10-hydroxyundecyl)-3,7-dmethylxanthine, 1-(11-Tetradecylamino-10-hydroxyundecyl)-3,7-dimethylxanthine, 1-[11-(4-Fluorobenzylamino )-10-hydroxyundecyl]-3,7-dimethylxanthine, 1-[11-(4-Trifluoromethylbenzylamino)-10-hydroxyundecyl]-3,7-dimethylxanthine, 1-[11-(3-Diethylaminopropylamino)-10-hydroxyundecyl]-3,7-dimethylxanthine, N,N'-bis[(10-yl-9-hydroxydecyl)-3,7-dimethylxanthine]-diaminododecane, 1-(14-Bromo-13-hydroxytetradecyl)-3,7-dimethylxanthine, 1-[11-(4-Aminobenzylamino)-10-hydroxyandecyl]-3,7-dimethylxanthine, 1-[11-(3,4,5-Trimethoxybenzylamino)-10-hydroxyundecyl]-3,7-dimethylxanthine, 1-[11-(3-Butoxypropylamino)10-hydroxyundecyl)-3,7-dimethylxanthine, 1-(14-Octylamino-13-hydroxytetradecyl)-3,7-dimethylxanthine, 1-(11-Propylamino-10-hydroxyundecyl)-3,7-dimethylxanthine, 1-(11-Undecylamino-10-hydroxyundecyl-3,7-dimethylxanthine, 1-(11-Phenylamino-10-hydroxyundecyl)-3,7-dimethylxanthine, N,N-bis [11-yl-10-hydroxyundecyl)-3,7-dimethylxanthine]undecylamine, 1-(11-Octadecylamino-10-hydroxyundecyl)-3,7-dimethylxanthine, 1-[9-(N-Methyloctylamino-8-hydroxynonyl)]-3,7-dimethylxanthine, 1-(4-Tetradecylamino-3-hydroxybutyl)-3,7-dimethylxanthine, 1-[9-(2-hydroxydecyl-1-amino)nonyl]-3, 7-dimethylxanthine, 1-(6-Octadecylamino-5-hydroxyhexyl)-3,7-dimethylxanthine, 1-[11-(N-Octylacetamido)10-hydroxyundecyl]-3,7-dimethylxanthine, 2-(11-Octylamino-10-hydroxyundecyl)-N-methylbenzamide, 1-(11-(N-Methyl-N-octylamino )-10-hydroxyundecyl)-3,7-dimethylxanthine, N-(11-Octylamino-10-hydroxyundecyl)-piperidine, 2-(11-Octylamino-10-hydroxyundecyl)-1,3-dihydroxybenzene, 1-[11-Amino-10-hydroxyundecyl)-3,7-dimethylxanthine, 1-(11-Hexadecylamino-10-hydroxyundecyl)-3,7-dimethylxanthine, 1-(11-Tridecylamino-10-hydroxylundecyl)-3,7-dimethylxanthine, 1-[11-Dihexylamino-10-hydroxyundecyl)-3,7-dimethylxanthine, 1-(11-Pentadecylamino-10-hydroxyundecyl)-3,7-dimethylxanthine, 1-[11-(N,N-Diethanolamino)undecyl]-3,7-dimethylxanthine, 1-[11-(2-Piperidinoethylamino)-10-hydroxyundecyl]-3,7-dimethylxanthine, 1-[11-(4-Methyl-1-yl-piperazino)-10-hydroxyundecyl]-3,7-dimethyxanthine, 1-[11-Hydroxy-10-aminoundecyl]-3,7-dimethylxanthine, 1-[11-(4-Chlorobenzyl)-10-hydroxyundecyl]-3,7-dimethylxanthine, 1-[11-(2,4,6-Trimethoxybenzylamino)-10-hydroxyundecyl]-3,7-dimethylxanthine, 1-(11-tert-Butylamino-10-hydroxyundecyl)-3,7-dimethylxanthine, 6-(11-dodecylamino-10-hydroxyundecoxy)-2-hydroxy-3,7-methylpurine, N,N-bis-[(11-yl-10-hydroxyundecyl)-3,7-dimethylxanthine]-dodecylamine, 1-[11-(3,4,5-Trimethoxyphenylamino)-10-hydroxyundecyl]-3,7-dimethylxanthine, 1-[11-(N-Methyl-N-dodecylamino)-10-hydroxyundecyl]-3,7-dimethylxanthine, 1-[11-(N-Dodecylacetamido)-10-hydroxyundecyl]-3,7-dimethylxanthine, 1-[11-(N-Tetradecylacetamido)-10-hydroxyundecyl]-3,7-dimethylxanthine, 1-[11-(3,4,5-Trimethoxybenzylacetamido)-10-hydroxyundecyl]-3,7-dimethylxanthine, 1-[11-(N-Dodecylacetamido) -10-acetoxyundecyl]-3,7-dimethylxanthine, 1 -[11-(N-Methyl-N-dodecylamino)-10-acetoxyundecyl]-3,7-dimethylxanthine, 1-[11-(Morpholine-4-yl)-10-hydroxyundecyl)-3,7-dimethylxanthine, 1-[11-(Dodecyl benzamido)-10-hydroxyundecyl]-3,7-dimethylxanthine, 1-[11-(3,5-Dimethoxybenzylamino)-10-hydroxyundecyl]-3, 7-dimethylxanthine, 1-[7-(3-Octyl-2-oxo-5-oxazolidinyl) heptyl]-3,7-dimethylxanthine, and 1-[9-(N-Dodecyl-2-oxazolidin-5-yl)nonyl]-3,7-dimethylxanthine.

6. The method for preventing development of MDR during cancer chemotherapy of claim 5 wherein the long chain amino alcohol compound is 1-(11-Dodecylamino-10-hydroxyundecyl)-3,7-dmethylxanthine.

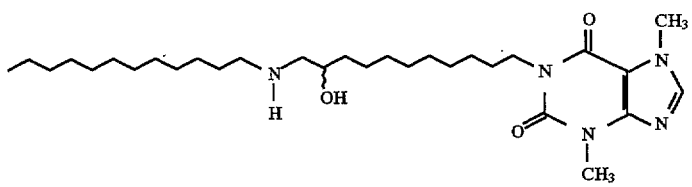

* * * * *